(12) United States Patent
Muthusamy et al.

(10) Patent No.: US 12,158,473 B2
(45) Date of Patent: *Dec. 3, 2024

(54) MULTIMERIC PROTEIN PURITY DETERMINATION

(71) Applicant: Regeneron Pharmaceuticals, Inc., Tarrytown, NY (US)

(72) Inventors: Kathir Muthusamy, Cheshire, CT (US); Jiann Kae Luo, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 827 days.

This patent is subject to a terminal disclaimer.

(21) Appl. No.: 16/686,770

(22) Filed: Nov. 18, 2019

(65) Prior Publication Data

US 2020/0166522 A1 May 28, 2020

Related U.S. Application Data

(63) Continuation of application No. 15/152,135, filed on May 11, 2016, now Pat. No. 10,520,511.

(Continued)

(51) Int. Cl.
*G01N 33/68* (2006.01)
*C07K 16/18* (2006.01)
(Continued)

(52) U.S. Cl.
CPC ......... *G01N 33/6854* (2013.01); *C07K 16/18* (2013.01); *C07K 16/468* (2013.01);
(Continued)

(58) Field of Classification Search
None
See application file for complete search history.

(56) References Cited

U.S. PATENT DOCUMENTS

2003/0106797 A1* 6/2003 Schneider ........ G01N 27/44726
204/461

FOREIGN PATENT DOCUMENTS

EP 1 803 814 A1 7/2007
EP 2009101 B1 10/2017
(Continued)

OTHER PUBLICATIONS

Brown et al., "Optimization of conditions for flow-through partial-filling affinity capillary electrophoresis to estimate binding constants of ligands to receptors," (2005) 540 Analytica Chimica Acta 403-410.

(Continued)

*Primary Examiner* — Rebecca M Giere
(74) *Attorney, Agent, or Firm* — Kramer Levin Naftalis & Frankel LLP

(57) ABSTRACT

Improved capillary zone electrophoresis (CZE), affinity capillary electrophoresis (ACE), and partially filled-ACE (PF-ACE) systems and methods for the detection and quantification of specific molecular entities in a mixture thereof are provided. During manufacturing, heterodimeric bispecific antibodies are often produced along with homodimer species, which can confound quantification of the bispecific antibody. Disclosed are capillary electrophoretic systems and methods of detecting a specific homodimer in the mixture of bispecific heterodimer and homodimers. A ligand capable of binding one of the subunits of the bispecific antibody is contacted with the mixture to form a complex having a reduced electrophoretic mobility, thereby enabling detection of the unbound homodimer.

14 Claims, 11 Drawing Sheets

Specification includes a Sequence Listing.

Related U.S. Application Data

(60) Provisional application No. 62/160,341, filed on May 12, 2015.

(51) Int. Cl.
    *C07K 16/46*      (2006.01)
    *G01N 21/33*      (2006.01)
    *G01N 21/64*      (2006.01)
    *G01N 27/447*    (2006.01)

(52) U.S. Cl.
    CPC ......... *G01N 21/33* (2013.01); *G01N 21/6428* (2013.01); *C07K 2317/31* (2013.01); *C07K 2317/526* (2013.01); *G01N 27/44726* (2013.01); *G01N 27/44795* (2013.01); *G01N 2201/06113* (2013.01)

(56) References Cited

FOREIGN PATENT DOCUMENTS

| WO | WO2001/85759 A1 | 11/2001 |
|---|---|---|
| WO | 2012162068 A2 | 11/2012 |
| WO | 2013064701 A2 | 5/2013 |
| WO | 2013136186 A2 | 9/2013 |
| WO | 2014078475 A2 | 5/2014 |
| WO | WO2015/033223 A2 | 3/2015 |

OTHER PUBLICATIONS

He et al., "Analysis of identity, charge variants, and disulfide isomers of monoclonal antibodies with capillary zone electrophoresis in an uncoated capillary column," (2010) 82(8) Anal. Chem. 3222-30.
He et al., "Rapid analysis of charge variants of monoclonal antibodies with capillary zone electrophoresis in dynamically coated fused-silica capillary," Journal of Separation Science, vol. 34: pp. 548-555 (2011).
Jorgenson and Lukacs, "Free-zone electrophoresis in glass capillaries," Clin Chem. Sep. 1981;27(9):1551-3.
Jorgenson and Lukacs, "Capillary zone electrophoresis," Science Oct. 21, 1983, vol. 222, Issue 4621, pp. 266-272.
Krylov and Dovichi, "Capillary Electrophoresis for the Analysis of Biopolymers," (2000) 72 Anal. Chem. 111-128.
Krylov, S., "Nonequilibrium Capillary electrophoresis of Equilibrium Mixtures (NECEEM): a Novel Method for Biomolecular Screening," (2006) 11(2) J Biomol Screen 115-122.
Nielsen, et al., "Separation of antibody—antigen complexes by capillary zone electrophoresis, isoelectric focusing and high-performance size-exclusion chromatography," (1991) J. Chromatography A, vol. 539 Issue 1 pp. 177-185; 1991.
Muthusamy, Kathir, et al. "Purity Analysis of Bispecific Antibodies by Affinity Capillary Electrophoresis" Oct. 7, 2013.
Muthusamy, Kathir, et al. "Purity Analysis of Bispecific Antibodies by Affinity Capillary Electrophoresis" Jan. 19, 2016.
Muthusamy, Kathir, et al. "Purity Analysis of Bispecific Antibodies by Affinity Capillary Electrophoresis" Sep. 2014.
Szabolcs Fekete et al: "Analytical strategies for the characterization of therapeutic monoclonal antibodies", Trac, Trends in Analytical Chemistry., vol. 42, Jan. 1, 2013 (Jan. 1, 2013), pp. 74-83.
Shuai Sherry Zhao et al: "Applications of capillary electrophoresis in characterizing recombinant protein therapeutics", Electrophoresis, vol. 35, No. 1, Nov. 22, 2013 (Nov. 22, 2013), pp. 96-108.
Yan He et al: "Rapid Analysis of Charge Heterogeneity of Monoclonal Antibodies by Capillary Zone Electrophoresis and Imaged Capillary Isoelectric Focusing" In: "Capillary Electrophoresis and Microchip Capillary Electrophoresis", Mar. 25, 2013 (Mar. 25, 2013), John Wiley & Sons, Inc., Hoboken, NJ, USA.
Ying Shi et al: "Development and validation of a rapid capillary zone electrophoresis method for determining charge variants of mAb", Journal of Chromatography B: Biomedical Sciences & Applications., fol. 906, Oct. 1, 2012 (Oct. 1, 2012), pp. 63-68.
International Search Report and Written Opinion for PCT/US2016/031899 (dated Sep. 8, 2016).
Espinosa-De La Garza Carlos Eduardo et al: "Capillary Electrophoresis Separation of Monoclonal Antibody Isoforms Using a Neutral Capillary", Journal of Visualized Experiments, vol. 119379155082, No. 119, Jan. 16, 2017 (Jan. 16, 2017), p. 55082, XP055827891, DOI: 10.3791/55082 Retrieved from the Internet: URL:https://www.ncbi.nlm.nih.gov/pmc/articles/PMC5352263/pdf/jove-119-55082.pdf>.
European Search Report EP 21 17 1963, dated Jul. 27, 2021.
Kempná, Petra et al. "Isoelectric point mobility shift assay for rapid screening of charged and uncharged ligands bound to proteins." IUBMB life vol. 55,2 (2003): 103-7. doi:10.1080/1521654031000095756.
Wheeler, Tobias D et al. "Microchip zone electrophoresis for high-throughput analysis of monoclonal antibody charge variants." Analytical chemistry vol. 86, 11 (2014): 5416-24. doi:10.1021/ac500497n.

\* cited by examiner

MULTIMERIC PROTEIN PURITY DETERMINATION

CROSS-REFERENCE TO RELATED APPLICATIONS

This application is a continuation of U.S. application Ser. No. 15/152,135, filed on May 11, 2016, which claims the benefit of priority under 35 USC § 119(e) of U.S. Provisional Patent Application No. 62/160,341, filed May 12, 2015, which application is herein specifically incorporated by reference in its entirety.

SEQUENCE LISTING

A WIPO Standard ST.25 (1998) compliant text file of a sequence listing is filed concurrently with the present specification. The contents of the text file are herein incorporated by reference. The text file containing the sequence listing is named "10141US01_ST25" was created on Apr. 11, 2016, and contains about 19,025 bytes of information.

BACKGROUND

Field

The invention is generally directed to compositions, systems and methods for detecting one or more species of polypeptide in a complex mixture of polypeptides and polypeptide complexes. Specifically, the invention includes compositions, systems and methods for detecting homodimers in a mixture of multimers that include bispecific antibodies.

Related Art

Monoclonal antibodies represent an important class of therapeutics for various diseases. There is a growing interest in increasing the versatility of monoclonal antibodies, with one approach being the design and generation of bispecific antibodies (bsAb). Conventional expression of a bsAb using two heavy and two light chains will result in multiple (up to ten) undesirable multimeric protein products due to the random association of heavy and light chains. Co-expression of two unique heavy chains and one common light chain will minimize the number of side products to two homodimeric species, which may need to be subsequently removed during purification. Thus, a need for effective and efficient methods to detect and differentiate homodimer side products from the desired heterodimer (bsAb) exists. Reagents and methods to estimate the purity of a bsAb consisting of two unique heavy chains and two identical light chains are disclosed.

SUMMARY

Applicants have developed reagents and processes to detect homodimer side products within a mixture of multimeric products. The reagents include a ligand that binds to a specific subunit of the homodimer side products. The processes include modified forms of capillary zone electrophoresis (CZE) called affinity capillary electrophoresis (ACE), in which the ligand is combined with the mixture of multimeric products prior to electrophoresis; and partially filled affinity capillary electrophoresis (PF-ACE), in which the capillary is partially filled with the ligand prior to electrophoresing the mixture of multimeric products. The multimeric products include a heterodimer, which contains a first subunit and a second subunit; a first homodimer, which contains two first subunits (a.k.a. "homo-B"); and a second homodimer, which contains two second subunits (a.k.a. "homo-A"). The ligand binds to a specific subunit, in some embodiments to the first subunit, and in other embodiments, the second subunit.

In one embodiment, the mixture of multimeric proteins is produced by cells containing heterologous nucleic acids that express the first subunit and the second subunit. In particular embodiments, the cells are mammalian cells used in the industrial scale production of biotherapeutic molecules like monoclonal antibodies. Cells include CHO cells and their derivatives—CHO-K1 cells and EESYR® cells.

In one embodiment, the homodimer (either the first homodimer or the second homodimer) is detected via capillary zone electrophoresis by decreasing the charge/mass ratio of the heterodimer and other homodimer. The charge/mass is decreased when one of the ligands binds to one of the subunits, resulting in the formation of a complex having a decreased charge/mass, which greatly slows the mobility of the complex through the capillary relative to the unbound subunit and its homodimer. For example, when the multimer mixture is combined with the ligand that binds to the second subunit (second ligand), that second ligand will bind to the heterodimer (which contains a first subunit and a second subunit) and the second homodimer (which contains two second subunits). The first homodimer remains unbound and therefore has a higher charge to size ratio and concomitant increased mobility through the capillary. Thus, during electrophoresis, the first homodimer peak is detected first and its peak is well separated from the complexed second homodimer and heterodimers. Likewise, when the multimer mixture is combined with the first ligand, the electrophoretic mobility of the complexed first homodimer and the heterodimer is decreased, allowing the second homodimer to be detected as a well separated peak. This procedure is called affinity capillary electrophoresis (ACE).

In another embodiment, the capillary is pre-loaded with the ligand plug. When the mixture of multimers is loaded and electrophoresed through the capillary, each multimer species will encounter the "ligand plug" in the capillary. Any multimer containing a subunit that binds to the ligand will bind the ligand and its electrophoretic mobility will be retarded (i.e., mobility shift). The unbound homodimer is then free to move through the capillary separated from the ligand-bound multimers. This procedure is called partially filled-affinity capillary electrophoresis (PF-ACE).

To detect both the first homodimer and the second homodimer, at least two separate procedures are performed, one using the first ligand to detect the second homodimer, and one using the second ligand to detect the first homodimer. Optionally, a standard CZE procedure may be run to detect the heterodimer, which having a similar charge/mass to both homodimers will be detected in the same "peak" as the homodimers. The heterodimer fraction is quantified by subtracting the first homodimer detected in the first ACE or PF-ACE procedure, and subtracting the second homodimer likewise detected in the second procedure.

In one embodiment, the first subunit contains an immunoglobulin CH3 domain that enables the first subunit to bind protein A, and the second subunit contains a variant immunoglobulin CH3 domain that does not enable the second subunit to bind protein A. In one embodiment, each homodimer is a monospecific antibody having a distinct specificity, and the heterodimer is a bispecific antibody specific for both the cognate antigen of the first homodimer and the cognate antigen of the second homodimer. In one embodiment, each of the three antibodies (e.g., bsAb or hetero-AB, homo-A, homo-B) contains identical light chains, and the first and second subunits refer to heavy chains. While the antibodies are referred to as homodimers and heterodimers, they are usually actually tetramers. Since the light chains are the same for each multimeric species, they are essentially ignored for the purposes of nomenclature. In a specific embodiment, the first heavy chain can bind to protein A, and the second heavy chain contains the H95R and Y96F substitutions of the CH3 domain, which abrogates protein A binding (numbering according to IMGT; see Lefranc, M.-P., (2008) 40 Mol. Biotechnol. 101-111).

In one embodiment, the ligand is an antibody that binds to a subunit. The first ligand is an antibody that binds to the first subunit, but not to the second subunit; and the second ligand is an antibody that binds to the second subunit, but not to the first subunit. In one embodiment, the pI (isoelectric point) of the ligand is different or modified to be different than the pI of each of the multimers (e.g., more acidic or lower pI).

DRAWINGS

DETAILED DESCRIPTION

Figure 1:
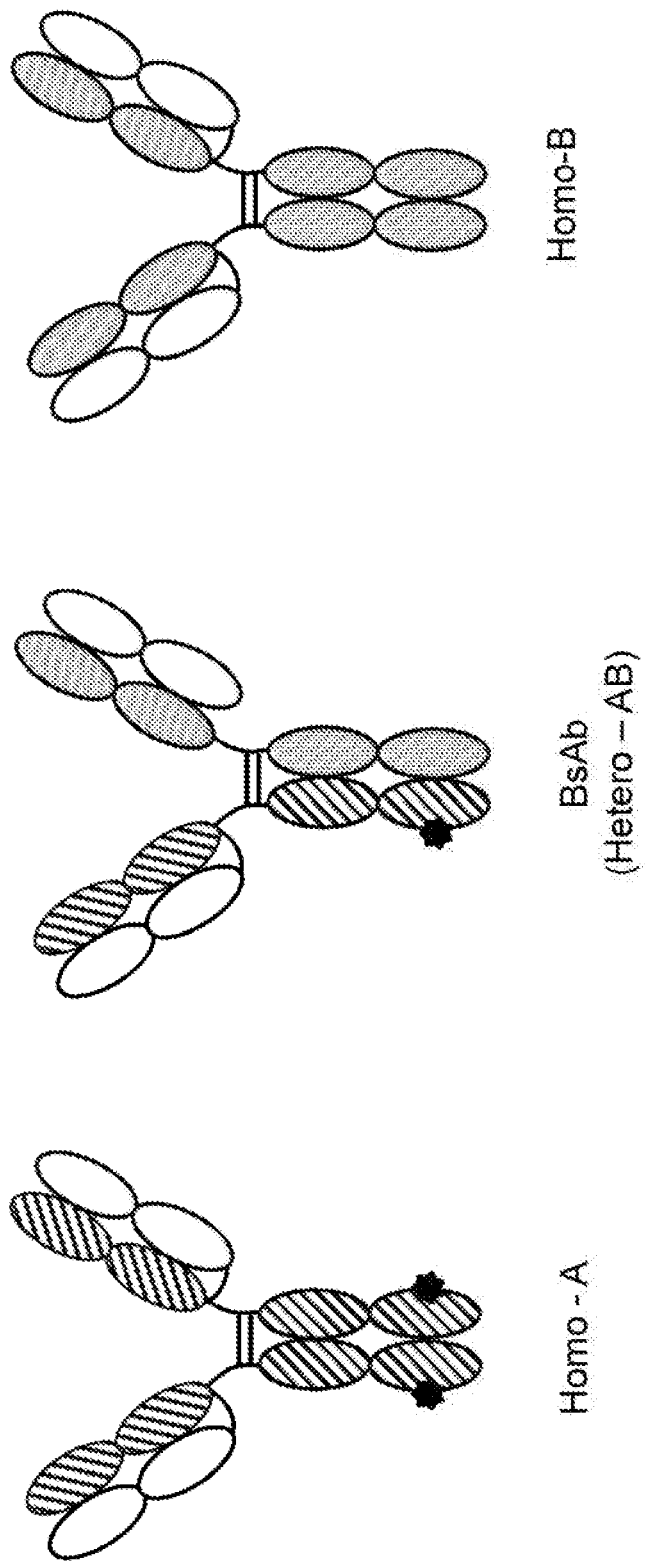
FIG. 1 is a schematic diagram depicting a bispecific antibody (hetero-AB) and the product-related side-products (homo-A and homo-B) expressed during production. The dipeptide substitution in the CH3 domain lacking protein A binding is indicated by the filled six-pointed star.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Although any methods and materials similar or equivalent to those described herein can be used in the practice or testing of the present invention, the preferred methods and materials are now described. All publications cited herein are incorporated herein by reference to describe in their entirety. Unless defined otherwise, all technical and scientific terms used herein have the same meaning as commonly understood by one of ordinary skill in the art to which this invention belongs.

As used herein, the term "ligand" means any molecule that binds to another molecule. "Ligand" has the traditional meaning in the biochemical arts as an agonist or antagonist that binds to a cognate receptor. "Ligand" as used herein also encompasses the antibody-antigen interaction, in which the antibody is the ligand and the antigen is its cognate binding partner, or vice versa in which the antigen is the ligand and the antibody (or fragment thereof) is the cognate binding partner.

A ligand may be any molecule that binds to a "cognate" molecule, including antibodies, antibody fragments, ScFv molecules, trap molecules, receptor concatamers, recombinant or synthetic molecules containing one or more CDRs, antigens, haptens, recombinant epitopes, canonical ligans, receptors, soluble receptor fragments, nuclear receptors, steroids, peptides, aptmers, RNAs, DNAs, organic molecules, small molecules, and the like.

The term "ligand plug" refers to a ligand-rich area within the capillary, generally near the loading end (e.g., near the anode end) of the capillary. The capillary can be pre-loaded with ligand, which forms a "plug" that binds to (i.e., "captures") the ligand's cognate binding partner as that cognate binding partner migrates along the capillary, forming a "complex" that has an altered mobility.

The term "complex" refers to and includes higher order molecular entities comprising at least two molecular entities, such as small molecules, metals, polypeptides, proteins, nucleic acids, aptamersor other molecular entities. The term "complex" includes multisubunit proteins. For example, hemoglobin is a complex containing two alpha globin chains, two beta globin chains, four iron-containing heme groups, and $CO_2$ or $O_2$. For example, a receptor bound to its cognate ligand is a complex, an antibody bound to an antigen is a complex, and an enzyme bound to a substrate or bound to a substrate and a cofactor is a complex. As used in some embodiments herein disclosed, "complex" includes a homodimer or heterodimer bound to a ligand. A complex may also be referred to as "molecular entity" or "entity". For example, a homodimer or heterodimer bound to its ligand, which is a complex, may itself be referred to as an "entity" or "molecular entity"

As used herein, the term "multimer" and the phrase "multimeric protein" are used interchangeably to denote a protein made of more than one component subunit. The subunits may be bound together or otherwise associated to form the multimer. The binding or association may be via any one or more intermolecular bonds, including covalent and non-covalent bonds. A "homodimer" is a multimer comprising two or more subunits that are the same or functionally equivalent. As used herein, a homodimer comprises at least two polypeptide chains that are the same or functionally equivalent, but the homodimer may include additional subunits as well. For example, a monoclonal antibody contains two identical heavy chains. As such, the monoclonal antibody may be considered to be a "homodimer". However, a complete canonical monoclonal antibody also contains two light chains and thus can be referred to as a tetramer. A "heterodimer" is a multimer comprising two or more subunits that are not the same or are not functionally equivalent. The heterodimer may contain additional subunits beside the two dissimilar subunits. For example, a bispecific antibody contains two heavy chains and two light chains, such that one half of the antibody (e.g., one heavy chain and one light chain) binds one epitope and the other half of the antibody (e.g., another heavy chain and the same light chain, the same heavy chain and another light chain, or another light chain and another heavy chain) specifically binds to another epitope. The bispecific antibody is a tetramer. In some cases, the bispecific is a heterodimer as that term relates to the heavy chains not being the same or not being functionally equivalent.

As used herein, the term "subunit" or "component subunit" or means a component of a multimer, usually (but not always) a polypeptide. The component polypeptide is a single chain and can be of any size from three amino acids to several thousands of amino acids long.

As used herein, the term "bind" or the term "bound" means the association one molecule with another through non-covalent forces. To bind or to be bound implies a relatively strong force (micromolar or below Kd), such as that between an antibody and its antigen, or a ligand and its receptor. Non-covalent forces include hydrogen bonding, ion-dipole and ion-induced dipole interactions, ionic interaction, Van der Waals forces, hydrophobic interaction, halogen bonding, pi-pi interactions, and cation pi-anion pi interaction. See Wang et al., (2001) 30 Ann. Rev. Biophys. Biomol Structure 211-243.

The term "attach", "crosslink", "attached", or "crosslinked" is generally used to convey the covalent association of two or more subunits to form a more complex protein.

The terms "CH3", "CH3 domain", and "immunoglobulin CH3 domain" are used interchangeably and denote the region of an immunoglobulin heavy chain spanning from about amino acid 341 to the C-terminus according to the EU numbering system (Edelman et al., (1969) 63(1) Proc. Natl. Acad. Sci. USA. 78-85). The CH3 domain is involved in protein A binding, such that for example the CH3 domains of human IgG1, IgG2, and IgG4 modulate protein A binding, but the CH3 domain of IgG3 does not (Van Loghem et al., *Staphylococcal protein A and human IgG subclasses and allotypes,* 15(3) Scand. J. Immunol. 275-8 (1982)). Amino acid substitutions H95R and Y96F in the CH3 domain (IMGT numbering; H435R and Y436F in the EU numbering system) abrogates protein A binding (U.S. Pat. No. 8,586,713 (issued Nov. 19, 2013)).

As used herein, the term "antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) 90 PNAS USA 6444-6448; and Poljak et al. (1994) 2 Structure 1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) 6 Human Antibodies and Hybridomas 93-101) and use of a cysteine residue, a marker peptide and a C-terminal polyhistidine tag to make bivalent and biotinylated scFv molecules (Kipriyanov et al. (1994) 31 Mol. Immunol. 1047-1058). Antibody portions, such as Fab and F(ab')2 fragments, can be prepared from whole antibodies using conventional techniques, such as papain or pepsin digestion of whole antibodies. Moreover, antibodies, antibody portions and immunoadhesion molecules can be obtained using standard recombinant DNA techniques commonly known in the art (see Sambrook et al., 1989).

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., (1991) 88 Proc. Natl. Acad. Sci. USA 10535; Byrn et al., (1990) 344 Nature 677; and Hollenbaugh et al., (1992) "Construction of Immunoglobulin Fusion Proteins", in Current Protocols in Immunology, Suppl. 4, pages 10.19.1-10.19.11. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to one or more ligand(s). For example, Fc-fusion protein is a trap, such as for example an IL-1 trap (e.g., rilonacept, which contains the IL-1RAcP ligand binding region fused to the IL-1R1 extracellular region fused to Fc of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. No. 7,087,411 (issued Aug. 8, 2006) and 7,279,159 (issued Oct. 9, 2007)).

The term "protein A" as used herein means natural forms, recombinant forms, modified forms, engineered forms and derivatives of the 42 kDa *Stapylococcus aureus* cell wall protein A that bind to the Fc domains of IgG1, IgG2 and IgG4, but not to IgG3 (Dima et al., (1983) 13(8) Eur. J. Immunol. 605-14). Engineered protein A may be for example a Z-domain tetramer, a Y-domain tetramer, or an engineered protein A that lacks D and E domains. These engineered protein A exemplars are unable to bind (or bind with very low affinity if at all) to the VH3 domain of an immunoglobulin, but can still bind to the CH3 domains of IgG1, IgG2 and IgG4. Engineered protein A is discussed in Minakuchi et al., (2013) 22(9) Protein Sci. 1230-8. Commercially available proteins include Mab Select® (GE Healthcare, Little Chalfont, UK), Mab Select Sure (GE Healthcare, Piscataway, NJ) Prosep Ultra® (Millipore, Billerica, MA), and Poros A® (Perspective Biosystems, Framingham, MA).

Protein A affinity chromatography makes use of the affinity of protein A for the Fc domain to purify Fc-containing proteins. In practice, protein A chromatography involves using protein A immobilized to a solid support. See Gagnon, *Protein A Affinity Chromotography, Purification Tools for Monoclonal Antibodies*, Validated Biosystems 155-198 (1996). The solid support is a non-aqueous matrix onto which protein A adheres. Such supports include agarose, sepharose, glass, silica, polystyrene, nitrocellulose, charcoal, sand, cellulose and any other suitable material. Methods for affixing proteins to suitable solid supports are well known in the art. See e.g. Ostrove, (1990) in Guide to Protein Purification, Methods in Enzymology, 182: 357-371. Such solid supports, with and without immobilized protein A, are readily available from many commercial sources such as Vector Laboratory (Burlingame, CA), Santa Cruz Biotechnology (Santa Cruz, Calif.), BioRad (Hercules, CA), Amersham Biosciences (part of GE Healthcare, Uppsala, Sweden), Pall (Port Washington, NY) and EMD-Millipore (Billerica, MA). Protein A immobilized to a pore glass matrix is commercially available as PROSEP®-A (Millipore). The solid phase may also be an agarose-based matrix. Protein A immobilized on an agarose matrix is commercially available as MABSELECT™ (GE Healthcare Bio-Sciences, Pittsburgh, PA).

The term "capillary" refers to a substrate through or upon which one or more molecular entities travel, in some cases at different rates to allow for separation. A capillary can be made of any material, such as glass or a polymer. For example, bare fused silica capillaries (40 or 50 μm) were used in some experiments exemplified below (available from Polymicro Technologies, Phoenix, AZ). A capillary can be a hollow tube of a length that is greater than its diameter. A capillary is generally used to separate biomolecules or other molecular entities based upon the mass and/or charge of the entity. For example, when an electric potential is placed across the capillary, the molecular entities migrate through the capillary at a rate determined by their charge to size ratio. To provide the electrical potential, one end of the capillary is linked to a cathode (negative charge) ("cathode end of the capillary") and the other end of the capillary is linked to an anode (positive charge) ("anode end of the capillary"). Positive-charged entities will migrate toward the cathode.

A "detector" or "detector window" is provided at a point along the long axis of the capillary, to serve as a window to detect molecular entities as they pass by. Molecular entities can be detected by any one or more of methods known in the molecule detection arts. For example, proteins can be detected by absorbance of electromagnetic radiation at 220 nm or 280 nm (DNA at 260 nm) ("UV absorbance detection"). See C. Stoscheck, (1990) 182 Methods in Enzymology 50-69. Laser-induced fluorescence (CE-LIF) may also be employed to detect molecular entities by native fluorescence (for those molecules having native fluorescence) or detection of labeled entities. For example, a 280 nm or 295 nm laser can be used to induce the natural fluorescence of tyrosine, tryptophan and phenylalanine of proteins, and the emitted light is detected (e.g., the Beckman Coulter PA 800 Protein Characterization System, Beckman Coulter, Brea, CA). Molecular entities may also be detected by LIF by derivatizing the entity with fluorophore tags, exciting the derivatized entity with a laser (e.g., argon-ion laser emitting at 488 nm, HeCd laser emitting at 442 nm, or diode laser emitting at 473, 410, 405, or 425 nm), and detecting the emission wavelength. Those tags include inter alia fluorescein isothiocyanate (FITC), carboxyfluorescein succinimidyl ester (CFSE), 6-oxy-(N-succininmidyl acetate)-9-(2-methoxycarbonyl) (SAMF), N-hydroxysuccinimidyl fluorescein-O-acetate (SIFA), 4-fluoro-7-nitro-2,1,3-benzoxadiazole (NBD-F), 3-(2-furoyl)quinoline-2-carboxaldehyde (FQ), 5-(4,6-dichrolotriazinyl)aminofluorescein (DTAF) and 3-(4-carboxybenzoyl)-2-quinolinecarbox-aldehyde (CBQCA). See E. Szökö & T. Tábi, (2010) 53(5) J. Pharma. and Biomed. Analysis 1180-1192.

The term "cell" refers to a prokaryotic or a eukaryotic cell. A cell is capable of expressing a polypeptide or protein that is useful inter alia as a reagent or as a therapeutic drug (Kipriyanov and Little, (1999) 12 Molecular Biotechnology 173-201). The expressed polypeptide or protein may localize within the cell, localize at the cell membrane or cell wall, or be secreted from the cell. Prokaryotic cells include bacterial cells like *Escherichia coli* (Spaduit et al., (2014) 32(1) Trends Biotechnol. 54-60). Eukaryotic cells include plant cells like tobacco, *Arabidopsis*, potato, maize, carrot, and safflower (Yusibov et al., (2011) 7:3 Human Vaccines 313-321; K. Ko, (2014) 33(3) Monoclonal Antibodies in Immunodiagnosis and Immunotherapy 192-198). Eukaryotic cells include yeast cells like *Saccaromyces cerevisiae* and *Pichia pastoris* (Spaduit, et al., (2011) 3(5) MAbs 453-60). Eukaryotic cells include insect cells like 519 cells (Huang et al., (2006) 26(2A) Anticancer Res. 1057-63). Eukaryotic cells include mammalian cells like BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, "CHO cells", CHO-K1 cells, EESYR® cells, NS-1 cells, MRC-5 cells, WI-38 cells, BHK cells, 3T3 cells, 293 cells, RK cells, Per.C6 cells and chicken embryo cells. A "Chinese hamster ovary (CHO) cell line" or one or more of several specific CHO cell variants, such as the CHO-K1 cell line are optimized for large-scale protein production, such as in the production of antibodies. The EESYR® cell line is a specialized CHO cell line optimized for enhance production of proteins of interest. For a detailed description of EESYR® cells, see U.S. Pat. No. 7,771,997 (issued Aug. 10, 2010).

The term "mobility" refers to the movement of a molecular entity (including a complex) through a medium. The medium can be a gel, a film, air or other gas, aqueous buffer or other liquid, a capillary, a thin film, sieving particles, or the like. The molecular entity may move through inter alia an electric field, a magnetic field, a gravitational field, by simple diffusion, or via molecular sieving. Mobility is generally related to the volume, mass, or charge of the molecular entity. For diffusion, a molecular entity having a larger mass has lower mobility than an entity or complex having a smaller mass. Mobility of a molecular entity in an electric field (i.e., "electrophoretic mobility") depends on the charge-to-mass ratio of the entity. The charge of the entity depends in part upon the three dimensional structure of the entity, its isoelectric point, its state of denaturation or nativity, its state of solvation and hydration, the buffer and pH of the medium. See Barroso et al., (2015) 854 Analytica Chimica Acta 169-177. The greater the charge to size ratio of the molecular entity, the greater the electrophoretic mobility (i.e., higher velocity through the medium).

Ligands

In one aspect, the invention provides a ligand that binds a first subunit of a multisubunit protein and does not bind a second subunit of the multisubunit protein. The ligand is used to identify those molecules that contain a first subunit, either directly or indirectly through subtraction. In an alternate embodiment, the ligand binds to the second subunit, and not the first subunit. Generally, the ligand binds to one subunit of a heterodimer, but not to the other subunit of the heterodimer.

In some cases, each of the first and second subunits contains an immunoglobulin CH3 domain. Since an immunoglobulin heavy chain contains a CH3 domain, each subunit may be an immunoglobulin heavy chain. The multisubunit protein therefore in some cases is an antibody containing two distinct heavy chains. Such an antibody can be a bispecific antibody having dual epitope specificity.

According to some protocols for producing bispecific antibodies (or other heteromultimers), the CH3 domain of one subunit is capable of binding to protein A (CH3), and the CH3 of the other subunit does not bind protein A or binds it at a much reduced affinity (CH3*). The bispecific antibody therefore binds protein A better than an antibody with two CH3 domains that having reduced or no protein A binding ability (i.e., CH3*), but not as well as the antibody with two protein A-binding CH3 domains. This differential binding to protein A can be used to separate the bispecific antibody from any homodimers that are present. In one embodiment, the CH3* comprises amino acid substitutions H95R and Y96F (numbered according to the IMGT exon numbering system), which reduce or abrogate protein A binding.

For example, a bispecific antibody can be produced by expressing in a cell (e.g., CHO cell or CHO cell-derivative such as EESYR®) both a first heavy chain specific to a first epitope, and a second heavy chain specific to a second epitope. Since the antibody contains two heavy chains, at least three forms of antibody would be produced by the cell: a homodimer specific to the first epitope having two identical first heavy chains (a.k.a. homo-B), a homodimer specific to the second epitope having two identical second heavy chains (a.k.a. homo-A), and a heterodimer specific to both epitopes and having both a first and a second heavy chain (a.k.a. hetero-AB). In some purification schema, the separation of the protein A-binding homodimer (homo-B) and the protein A-binding heterodimer (hetero-AB) is less than perfect and the resultant heterodimer (e.g., bispecific antibody) is contaminated with homodimer.

One particular object of the invention is to determine the purity of heterodimer produced by cells and purified by protein A chromatography by distinguishing the homodimers from the heterodimer. In some cases, the biophysical attributes of the homodimers and the heterodimer (Ab) (e.g., mass, isoelectric point, amino acid content, and the like) are similar enough to make specific identification and quantification of each species difficult. The ligand (L) is therefore used to selectively bind one of the homodimers and the heterodimer, and not bind the other homodimer. Such binding forms a complex (a.k.a. Ab·L) that has altered and distinguishing biophysical attributes, which enables the skilled artisan to distinguish the non-bound homodimer from the bound homodimer and bound heterodimer. In some cases the complex has altered electrophoretic mobility, which allows for greater separation or resolution of the uncomplexed homodimer from the ligand-associated complexes.

The ligand may be an antibody, antibody fragment, or other antigen-binding protein that specifically binds to one of the subunits (e.g., either the first subunit or the second subunit, but not both). In one embodiment, wherein (a) the heterodimer is a bispecific antibody, (b) the first subunit is an immunoglobulin heavy chain containing the CH3 domain that binds protein A, (c) the second subunit is an immunoglobulin heavy chain containing the CH3 domain that does not bind protein A (e.g., the CH3* containing the H95R and Y96F amino acid substitutions), and (d) the ligand is an antibody that binds the first subunit, the ligand comprises heavy chain complementarity determining regions (HCDR) 1, 2 and 3 comprising the amino acid sequences set forth in SEQ ID NO:1, SEQ ID NO:2, and SEQ ID NO:3, respectively, and/or light chain complementarity determining regions (LCDR) 1, 2 and 3 comprising the amino acid sequences set forth in SEQ ID NO:4, SEQ ID NO:5, and SEQ ID NO:6, respectively (e.g., anti-B antibody).

In another embodiment, wherein (a) the heterodimer is a bispecific antibody, (b) the first subunit is an immunoglobulin heavy chain containing the CH3 domain that binds protein A, (c) the second subunit is an immunoglobulin heavy chain containing the CH3 domain that does not bind protein A (e.g., the CH3* containing the H95R and Y96F amino acid substitutions), and (d) the ligand is an antibody that binds the second subunit, the ligand comprises heavy chain complementarity determining regions (HCDR) 1, 2 and 3 comprising the amino acid sequences set forth in SEQ ID NO:7, SEQ ID NO:8, and SEQ ID NO:9, respectively, and/or light chain complementarity determining regions (LCDR) 1, 2 and 3 comprising the amino acid sequences set forth in SEQ ID NO:10, SEQ ID NO:11, and SEQ ID NO:12, respectively (e.g., anti-B antibody).

System for Detecting or Quantifying Bispecific Antibodies

Bispecific antibodies (bsAbs) possess two distinct binding specificities, and have a wide range of clinical applications, including cancer therapy (Kufer et al., (2004) 22(5) Trends Biotechnol. 238-44; and Lameris et al., (2014) S1040-8428 (14) Crit. Rev. Oncol. Hematol. 2014, 00135-8.) BsAbs can cross-link and activate heterodimeric receptors, which are otherwise challenging to activate via traditional combination drug therapy or monotherapy (J. R. Cochran, (2010) 2(17) Sci Transl Med. 17ps5).

The manufacture of bsAbs at commercial scale is challenging. Multiple approaches have been adopted to generate viable bsAbs suitable for therapeutic use (R. E. Kontermann (2012) 4:2 MAbs 182-97). One such approach involves the use of a common light chain covalently linking two unique heavy chains (chain-A and chain-B) (Davis et al., PCT App. No. WO2010151792, Dec. 29, 2010; 2011; Babb et al., PCT App. No. WO2013184761, Dec. 12, 2013). The first heavy chain (a.k.a. "first subunit", or "chain-B"), the second heavy chain (a.k.a. "second subunit", or "chain-A") and the common light chain are co-expressed during production and are then assembled into three products: homo-A, homo-B and hetero-AB. Homodimers (homo-A or homo-B), consist of two identical heavy chains (AA or BB) and two identical light chains. The bsAb product (hetero-AB) consists of two unique heavy chains (chain-A and chain-B) and two identical light chains. Theoretically, the three products should be expressed in a ratio or 1:2:1 (homo-A, hetero-AB and homo-B) (FIG. 1). One of the heavy chains, chain-A, abrogates binding to protein A and it allows selective purification of the bsAb (hetero-AB), resulting from intermediate binding affinity to protein A column when compared to the tighter binding of homo-B, or the weaker binding of homo-A monospecific Abs.

Despite all these advances in the manufacturing of bsAbs, small amounts of homodimers (homo-A and homo-B) could still be present in purified bsAb drugs. Depending on its target antigen, even a small amount of homodimer could potentially exhibit a different mode of action or different degradation pathway and hence impact potency and immunogenicity of the bsAb product (Woods et al., (2013) 5 mAbs 711-722). Therefore, it is critical to develop an analytical method to assess the purity of bsAbs.

The structural and physiochemical similarities between the homodimeric product impurities and heterodimer make separation and quantification extremely difficult. Traditional separation-based purity assays such as gel electrophoresis and size-exclusion chromatography lack the resolution to distinguish bsAbs from their homodimeric impurities. Recently, an LC-MS based approach to estimate the purity of bsAb has been reported (Id.). Although mass spectrometry is routinely applied in characterizing the purity of bsAbs, its application to quantify bsAbs over homodimers involves modifications such as deglycosylation. Heterogeneity arising from ionization velocity and truncation of C-terminal lysine further limits the application of mass spectrometry for the purity assessment of bsAbs.

Capillary Electrophoresis (CE) is used to characterize antibodies (Jorgenson et al., (2000) 72 Anal. Chem. 111-128). Forms of CE include capillary electrophoresis-sodium dodecyl sulfate (CE-SDS), capillary iso-electric focusing (cIEF) and capillary zone electrophoresis (CZE). The separation mechanism of CZE is based on charge to size ratio. CZE is employed in some antibody assays using uncoated capillaries (He et al., (2010) 82(8) Anal. Chem. 3222-30).

Also, CZE combined with partially-filled affinity capillary electrophoresis (PF-ACE) has been used to determine the identity of particular molecular species (Brown et al., (2005) 540 Analytica Chimica Acta 403-410). PF-ACE takes advantage of the shift in mobility of the analyte (e.g., bsAb, homo-A and homo-B) due to its selective affinity towards chain specific ligands. PF-ACE can be employed orthogonal to the existing LC-MS based approach (Woods, 2013).

In another aspect, the invention provides a system, e.g. a CZE system, comprising a ligand, a first homodimer, a second homodimer, a heterodimer, a capillary, a detector, an anode at or near one end of the capillary, a cathode at or near the other end of the capillary, and a power supply. In one embodiment, the first homodimer comprises at least two identical first subunits (e.g., immunoglobulin heavy chains capable of binding to protein A), the second homodimer comprises at least two identical second subunits (e.g., immunoglobulin heavy chains incapable of binding to protein A), and the heterodimer comprises one first subunit and one second subunit. The detector can be positioned anywhere along the capillary. Generally, the molecular entities will have an overall positive charge and therefore migrate toward the cathode under an electric field. Therefore, in some embodiments, the detector is positioned near the cathode end of the capillary. The detector can detect protein and may employ inter alia a UV detection method, in which light absorbance at 210 nm or 280 nm is measured, or laser induced fluorescence, in which native fluorescence or fluorescent labels are detected.

In one embodiment, the ligand (which is specific for either the first subunit or the second subunit, but not both), the first homodimer, the second homodimer, and the heterodimer are loaded onto the capillary at or near the anode end of the capillary. In some cases, the mixture can be loaded near the cathode end or at any position along the capillary. The ligand binds to its cognate subunit and forms a complex with the heterodimer and one of the homodimers, but not the other homodimer. Thus, when the ligand binds to the first subunit, complexes comprising the first homodimer and the ligand (first complex), and the heterodimer and the ligand (second complex) are formed. Alternatively, when the ligand binds to the second subunit, complexes comprising the second homodimer and the ligand (third complex), and the heterodimer and the ligand (fourth complex) are formed. In each case, the complexes have a lower electrophoretic mobility than the unbound (uncomplexed) homodimer. In some embodiments, i.e., when the heterodimer is a bispecific antibody, the first subunit is an immunoglobulin heavy chain that is capable of binding protein A, and the second subunit is an immunoglobulin heavy chain that is incapable of binding protein A (i.e., containing the H95R and Y96F substituted CH3* domain.)

According to this system and method, the complexes are retarded during progression through the capillary and do not cross the detector window at the same time as the uncomplexed homodimer. The uncomplexed homodimer is therefore detected and quantified free of any interfering heterodimer and other homodimer. In the case of bispecific antibodies, one ACE assay uses the ligand that binds to the unsubstituted CH3 heavy chain, in which the CH3*:CH3* (homo-A) dimer remains uncomplexed. The CH3*:CH3* (homo-A) homodimer is detected and quantified. The other independent ACE assay (which may be run separately and/or in parallel to the first ACE assay) uses the ligand that binds to the H95R and Y96F substituted CH3* domain. Here, the CH3:CH3 (homo-B) dimer remains uncomplexed and is detected and quantified. In the embodiment in which both ACE assays are run, both homodimers can be quantified. Here, the bispecific heterodimer can be quantified by subtracting the quantity of each homodimer determined by the independent ACE assays from the total amount of dimer (CH3:CH3+CH3:CH3*+CH3*:CH3*) (homo-B+hetero-AB+homo-A) determined in a CZE assay without any ligand or using a standard curve that was generated for spiked homo-A and/or homo-B samples.

The system and method in another embodiment uses a ligand plug inserted near the anode (loading) end of the capillary, between the loading port and the detector (PF-ACE). Here, the multimer mixture (comprising first homodimer, second homodimer, and heterodimer) is loaded onto the capillary in front of the ligand plug. As the multimers migrate through the capillary, the constituent molecular entities encounter the ligand plug, at which point ligand-multimer complexes form, thereby reducing electrophoretic mobility of all species except those homodimers that do not bind the ligand. When the ligand binds the first subunit, the homodimer comprising two second subunits (and no first subunit) remains unbound and has unaffected electrophoretic mobility.

According to some embodiments in which the heterodimer is a bispecific antibody, the first subunit is an immunoglobulin heavy chain capable of binding protein A (a.k.a. subunit-B), and the second subunit is an immunoglobulin heavy chain containing a H95R and Y96F substituted CH3 domain (i.e., CH3*) (a.k.a. subunit-A), the ligand that binds to the first subunit is an antibody comprising heavy chain complementarity determining regions (HCDR) 1, 2 and 3, which comprise the amino acid sequences set forth in SEQ ID NO:1, SEQ ID NO:2, and SEQ ID NO:3, respectively, and comprising light chain complementarity determining regions (LCDR) 1, 2 and 3, which comprise the amino acid sequences set forth in SEQ ID NO:4, SEQ ID NO:5, and SEQ ID NO:6, respectively. Here, the ligand that binds to the second subunit is an antibody comprising heavy chain complementarity determining regions (HCDR) 1, 2 and 3, which comprise the amino acid sequences set forth in SEQ ID NO:7, SEQ ID NO:8, and SEQ ID NO:9, respectively, and comprising light chain complementarity determining regions (LCDR) 1, 2 and 3, which comprise the amino acid sequences set forth in SEQ ID NO:10, SEQ ID NO:11, and SEQ ID NO:12, respectively.

EXAMPLES

Example 1: Purity by Capillary Zone Electrophoresis (CZE)

Figure 2:
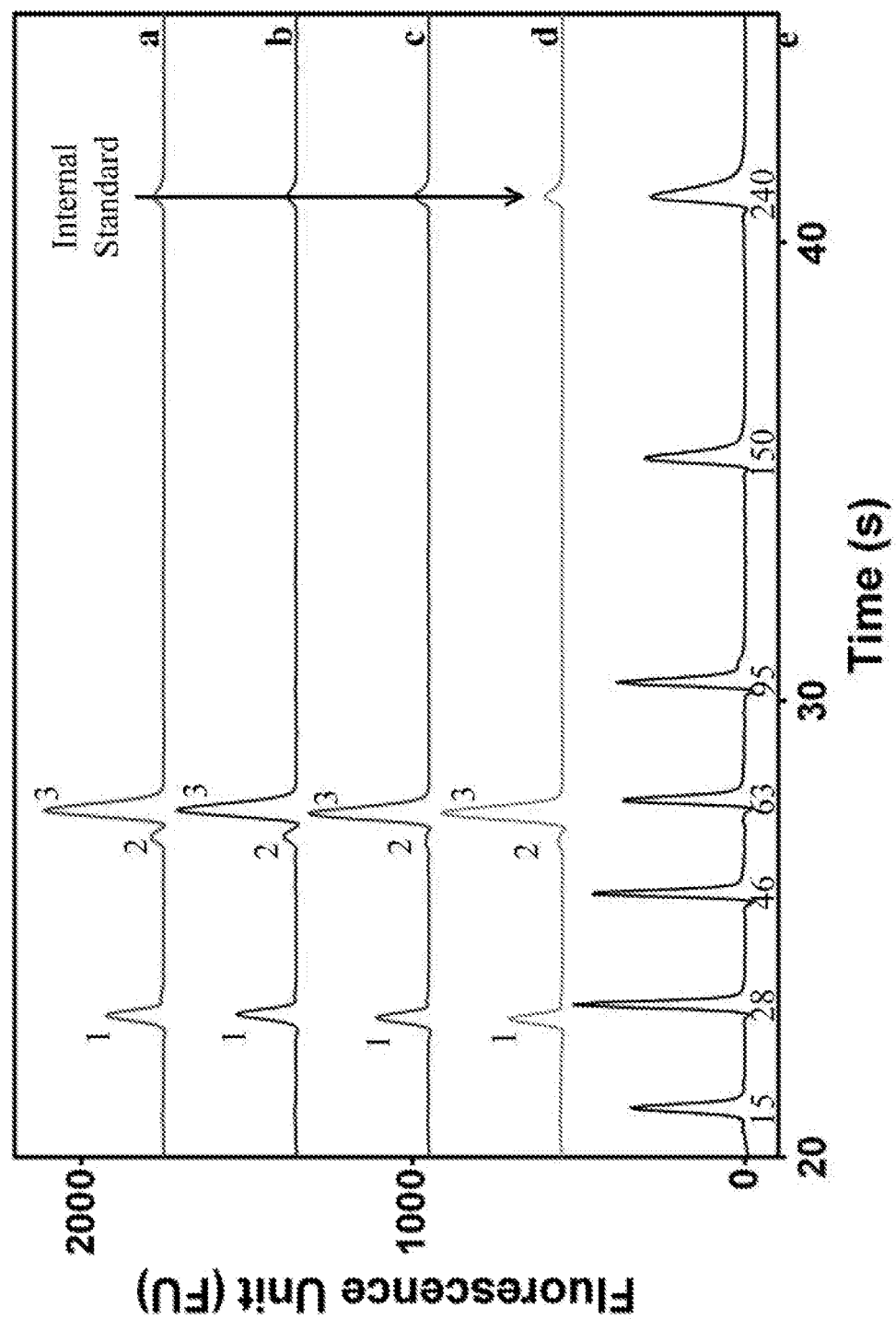
FIG. 2 depicts electropherograms of homo-A (a), homo-B (b), bsAb1 (c), mixture of homo-A, homo-B, and bsAb (d) and a molecular weight ladder (e) analyzed by CE-SDS under reducing conditions.

To evaluate the purity of a bispecific antibody ("bsAb"), CE-SDS was performed under reduced conditions. CE-SDS results obtained for bsAb (heterodimer), homo-A (second homodimer) and homo-B (first homodimer) samples (FIG. 2, traces a-c) under reduced conditions revealed three peaks corresponding to light chain (FIG. 2, peak-1), non-glycosylated heavy chain (FIG. 2, peak-2) and heavy chain (FIG. 2, peak-3). Co-mixture sample of homo-A:bsAb1:homo-B (1:2:1 molar ratios) that was prepared by spiking homo-A and homo-B to the purified bsAb1 also resulted in three peaks with similar migration times (FIG. 2, trace d). The electropherograms for bsAb, homodimers and their co-mixture were not distinguishable, indicating a limitation of this size based separation method (FIG. 2). Similar results were observed for CE-SDS under non-reducing conditions. These results are not surprising as the antibodies tested possess very similar molecular weights. Adequate separation selectivity is critical to resolve these homodimeric components from bsAb.

Figure 3:
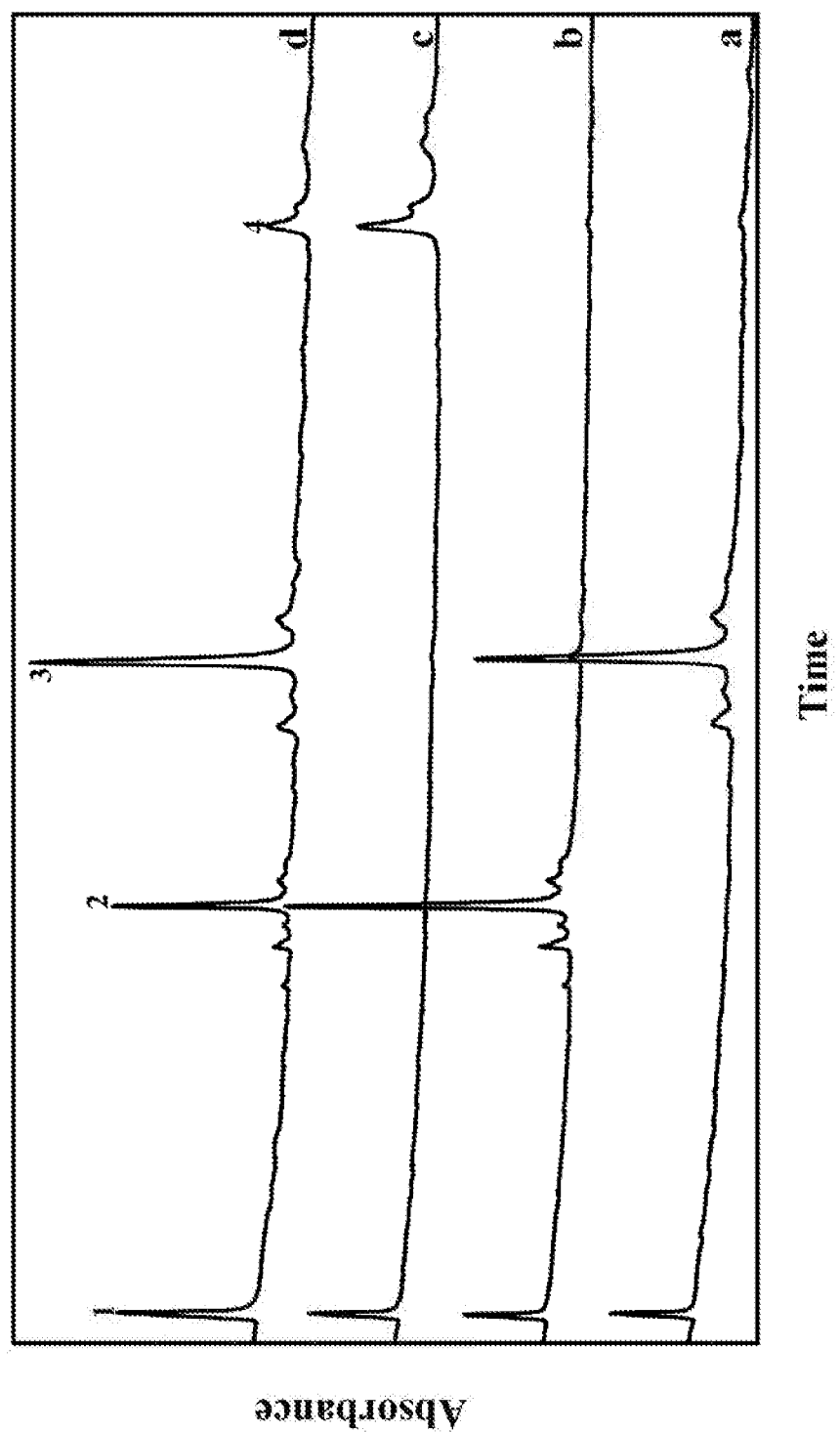
FIG. 3 depicts representative electropherograms of bsAb1 (trace a), homo-B mAb (trace b), homo-A mAb (trace c) and a 1:2:1 mixture of homo-A:bsAb1:homo-B (traced) separated via CZE.

CZE has been proven to be a powerful tool to resolve closely related mAbs (He, 2010). Purity of bsAb1 was assessed by CZE, a method that separates analytes based on their charge to size ratio. Analytes with a greater charge to size ratio migrate faster through the capillary. Relative to the pure bsAb-1 sample (FIG. 3, trace a), homo-A, with a larger charge to size ratio, migrates faster through the capillary (FIG. 3, trace b). Homo-B, with a lower charge to size ratio, migrates slower through the capillary (FIG. 3, trace c). As bsAb contains one arm of the heavy chain from homo-A (chain-A), and the other from homo-B (chain-B), and has a corresponding pI (8.01), the electrophoretic mobility of the bsAb lies between homo-A and homo-B (FIG. 3, trace a). The main peak group 2, 3 and 4 correspond to the homo-A, bsAb, and homo-B respectively. The minor peaks observed in the electropherograms arise from either charge variants or size variants of antibodies. A mixture of homo-A, bsAb, and homo-B (1:2:1 ratio) was made by spiking homo-A and homo-B to the purified bsAb. The mixture was then analyzed by CZE. The CZE trace of the mixture contains four sets of peaks, representing homo-A (peak group-2), bsAb (peak group-3), and homo-B (peak group-4) (FIG. 3, trace-d). The lower peak intensity observed for homo-B peak could be attributed to a combination of slower electrophoretic mobility and multiple charge variants of homo-B species that are distributed across the electropherogram. The co-mixture of homo-A:bsAb1:homo-B, that had no separation in CE-SDS (FIG. 2) showed promising results in CZE. The CZE profile for the bsAb1 (FIG. 3) is well resolved and thus the identification and quantification of purity is promising. CE-SDS separation was performed on an Agilent Bioanalyzer using Agilent Protein 230 kit.

Example 2: Purity by Partial-Filled Affinity Capillary Electrophoresis

Figure 4:
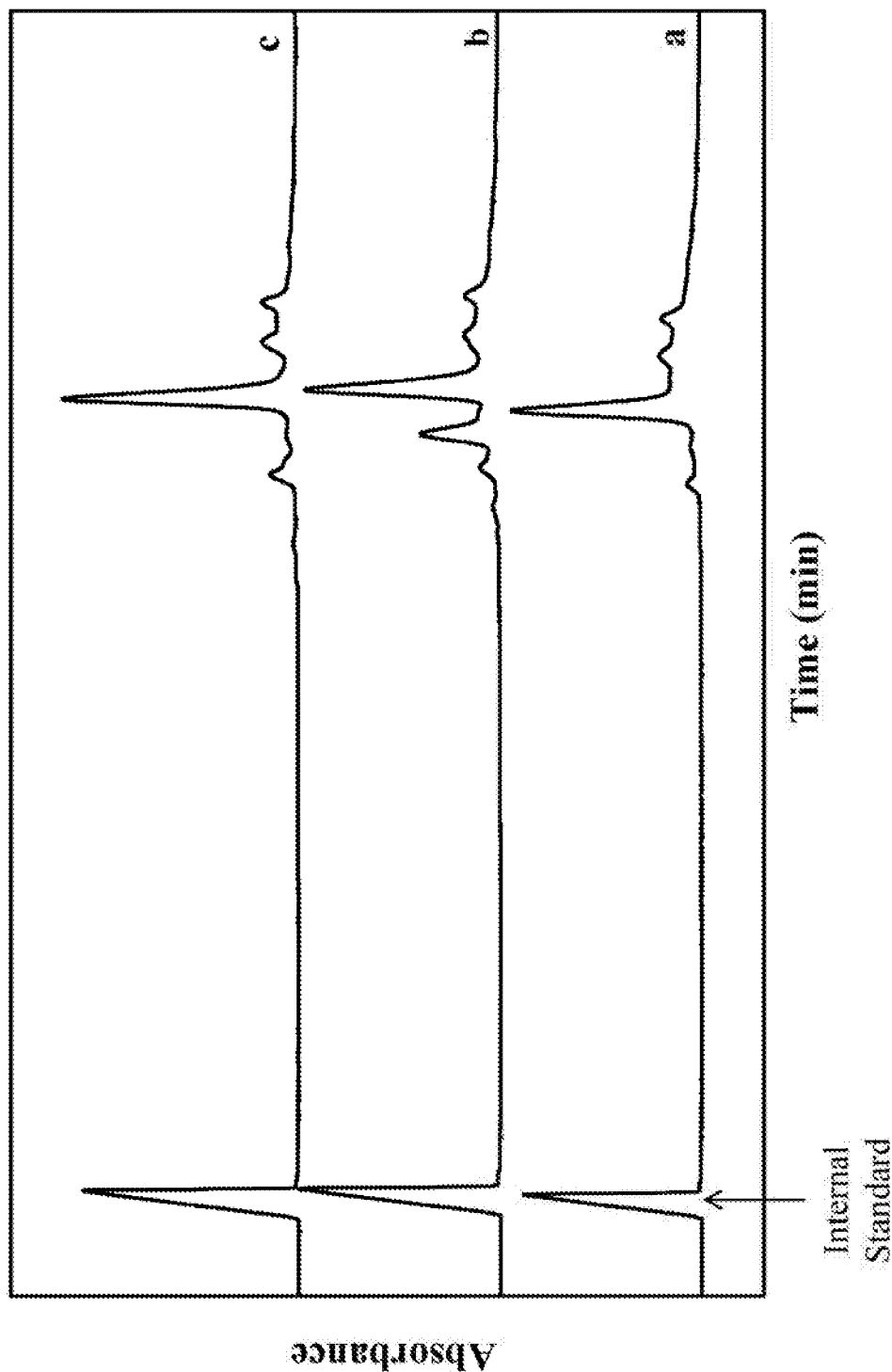
FIG. 4 depicts CZE electropherograms of bsAb2 (trace a), homo-B (trace b), and homo-A (trace c) mAbs.

The CZE is limited to samples containing entities with diverse charge to size ratios. Since this is not always the case, CZE cannot be applied to many bsAb candidates. For instance, bsAb2 and related homodimers possess similar pIs and size, and hence share very similar CZE profiles (FIG. 4, traces a-c). Due to lack of separation of the various molecular entities, identification of individual component molecular species was not practical.

Another viable approach to quantify purity is affinity capillary electrophoresis (ACE). In ACE, a mixture of an antibody (Ab) and a ligand (L), which forms an antibody-ligand complex (Ab·L), is prepared (see equation 1). The mixture is then injected into the capillary and electrophoresed. ACE is based on the differences in electrophoretic mobility between Ab, L and Ab·L. When either antigen or a chain specific antibody is used as a ligand, the homodimer quantification becomes independent of baseline resolution between various species. The selective mobility shift of individual species can be used to estimate the amount of any residual homodimers.

$$Ab + L \rightleftharpoons Ab \cdot L \tag{1}$$

In ACE, an antigen can be used as a ligand for a cognate antibody. Alternatively, a chain specific antibody (anti-A or anti-B) can be used as the ligand for the cognate antibody. Anti-A antibody (a.k.a., "second ligand") binds specifically to an antibody that contains chain-A (homo-A and bsAb).

Similarly, anti-B antibody (a.k.a., "first ligand") binds to an antibody containing chain-B (homo-B and bsAb).

In one embodiment, the anti-A antibody comprises heavy chain and light chain CDRs having amino acid sequences of SEQ ID NOs:7-12. In one embodiment, the anti-A antibody comprises a heavy chain variable region comprising the amino acid sequence of SEQ ID NO:13, and a light chain variable region comprising the amino acid sequence of SEQ ID NO:14. In one embodiment, the anti-A antibody comprises an immunoglobulin heavy chain comprising the amino acid sequence of SEQ ID NO:15, and an immunoglobulin light chain comprising the amino acid sequence of SEQ ID NO:16.

In one embodiment, the anti-B antibody comprises heavy chain and light chain CDRs having amino acid sequences of SEQ ID NOs:1-6. In one embodiment, the anti-B antibody comprises a heavy chain variable region comprising the amino acid sequence of SEQ ID NO:17, and a light chain variable region comprising the amino acid sequence of SEQ ID NO:18. In one embodiment, the anti-A antibody comprises an immunoglobulin heavy chain comprising the amino acid sequence of SEQ ID NO:19, and an immunoglobulin light chain comprising the amino acid sequence of SEQ ID NO:20.

In one embodiment, the theoretical isoelectric points (pIs) of chain-A-specific and chain-B-specific antibodies are 6.55 and 6.64 respectively. Peaks arising from analytes (bsAb or homodimers) that possess a similar pI and size could co-migrate with chain-specific mAbs and interfere with the identification and quantification. To avoid this potential interference, the electrophoretic mobilities of chain specific antibodies were modified through biotinylation. The EZ-Link™ Sulfo-NHS-Biotin kit and procedure (Thermo Scientific, Rockford, IL) were used to biotinylate anti-A and anti-B antibodies (Daniels and Amara, (1998) 296 Methods Enzymol. 307-18; Thermo Scientific, *Instructions: EZ-Link™ Sulfo-NHS-biotin*, Doc. No. 1850.3, available at https://tools.lifetechnologies.com/content/sfs/manuals/MAN0011580_EZ_Sulfo_NHS_Biotin_UG.pdf, Apr. 29, 2015). Several different NHS esters of biotin with varying properties and spacer arm lengths are available. Briefly, N-Hydroxysuccinimide (NETS) esters of biotin (e.g., Sulfo-NHS-Biotin, which is water soluble) were reacted in pH 7-9 buffers with primary amino groups (—NH2) of lysine and those available at the N-termini of each polypeptide.

Biotinylation via primary amine coupling and lysine side chain modification altered the charge of the chain specific antibodies towards the acidic and therefore their electrophoretic velocities were reduced, resulting in loss of detectable signal within experimental run time. The absence of any detectable peaks from chain specific antibodies made the identification and quantification of molecular species of interest straightforward.

Figure 5:
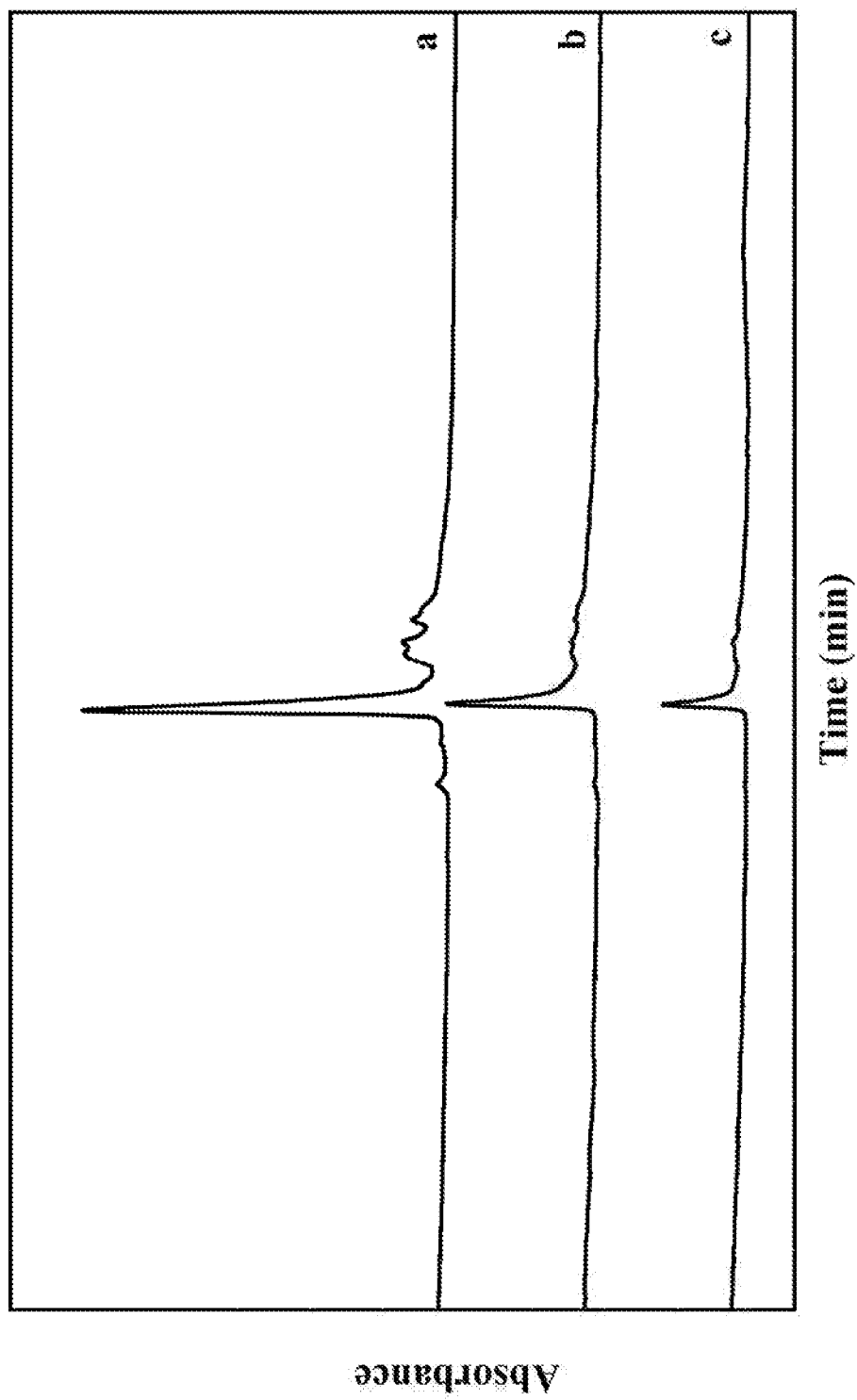
FIG. 5 depicts electropherograms of bsAb3 (trace A) samples, bsAb3 in the presence of anti-A mAb (trace B), and bsAb3 in the presence of anti-B mAb (trace C) affinity ligand.
Figure 6:
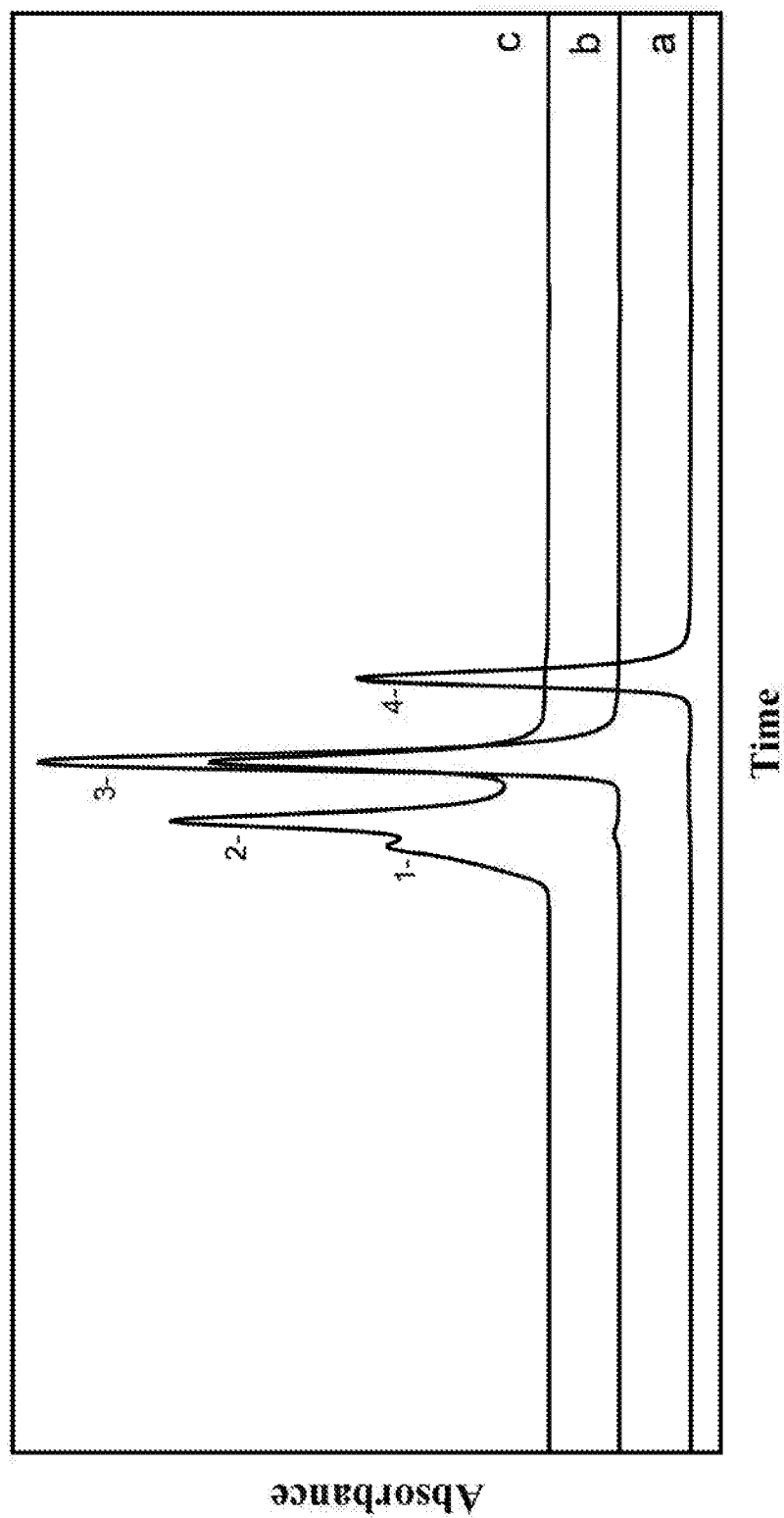
FIG. 6 depicts a SE-HPLC chromatogram depicting the stoichiometric binding of the chain-B specific ligand to the bsAb3. Trace a depicts bsAb3, trace b depicts anti-B antibody, and trace c depicts the combination of bsAb3 and anti-B antibody.

For ACE analysis, either anti-A or anti-B antibodies were used as ligands. ACE was performed using a bsAb-ligand complex prepared by mixing bsAb3 and anti-A or anti-B antibodies at a molar ratio of 1:2. Upon complex formation, the electrophoretic mobility of bsAb3 was expected to be modified, and it was anticipated that no residual signal of free bsAb3 would remain. However, for bsAb3-anti-A and bsAb3-anti-B complexes large amounts of residual peaks were detected at a similar migration time to that of free bsAb3 (FIG. 5, traces b and c). ACE data obtained for various ratios of bsAb and anti-B complexes (1:0.5, 1:1 and 1:3) demonstrated that the residual peak was seen even in the presence of excess anti-B ligand. To further investigate if residual unbound bsAb3 was present in the bsAb3-anti-B complex preparation, an SE-HPLC experiment was performed where good resolution between bsAb3 (FIG. 6, trace a; peak 4) and anti-B (FIG. 6, trace b; peak 3) was noted. SE-HPLC results indicate the presence of bsAb3-anti-B complex (FIG. 6, trace c; peaks 1 and 2) and excess anti-B (FIG. 6, trace c; peak 3). However, there is little to no evidence for the presence of any unbound bsAb3. These results suggest that the presence of residual peaks in high levels could be attributed to the dissociation of analyte-ligand (e.g., bsAb·L→bsAb+L) at high voltage applied during CZE experiments (FIG. 5). Dissociation of analyte-ligand complex has been previously reported in affinity-based separation methods such as CE (S. Krylov, (2006) 11(2) J Biomol Screen 115-122). Previous attempts to separate an equilibrium mixture containing ssDNA and ssDNA binding protein in a capillary was found to undergo continuous dissociation resulting in peaks and exponential "smears". Both ligand and target were dissociated throughout the electrophoresis (Id). For some bsAbs, the presence of residual peaks and "smears" observed in ACE analysis interferes with purity analysis.

To circumvent the dissociation effects, Partial-Filled Affinity Capillary Electrophoresis (PF-ACE) was developed and utilized (Brown et al., 540 Analytica Chimica Acta 403-410(2005)). PF-ACE is performed by partially filling the capillary with the ligand prior to sample injection. As the analytes migrate through the affinity ligand zone, a ligand-analyte complex is formed and its mobility is shifted compared to free analyte. The mobility of any residual analyte that does not bind the affinity ligand remains unchanged. PF-ACE can therefore provide an accurate estimate of the relative abundances of any residual analyte present in a bsAb.

Figure 7:
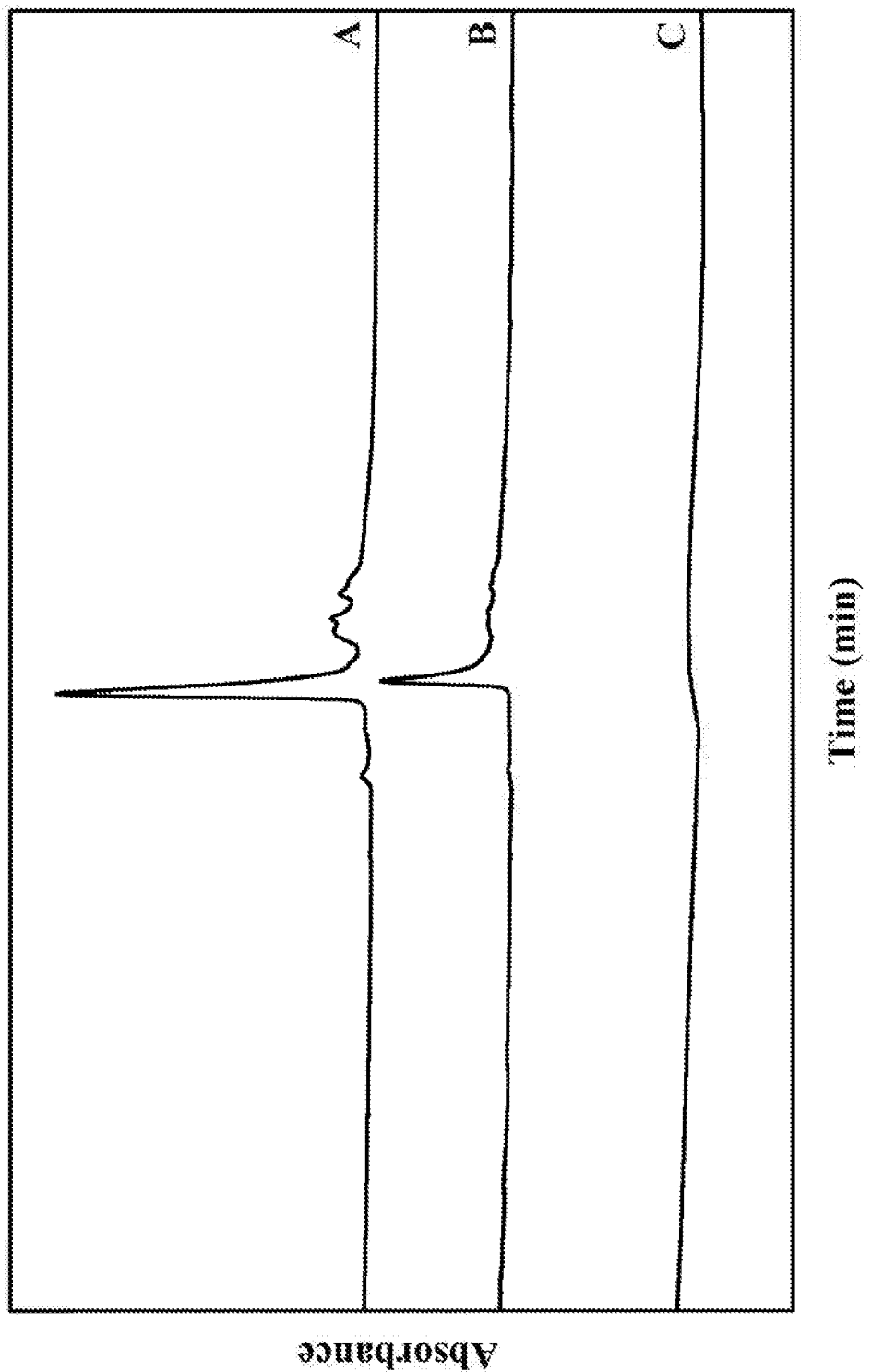
FIG. 7 depicts electropherograms of bsAb-3 (trace A) samples, in the presence of anti-chain B ligand under ACE (trace B) and PF-ACE (trace C) conditions.
Figure 8:
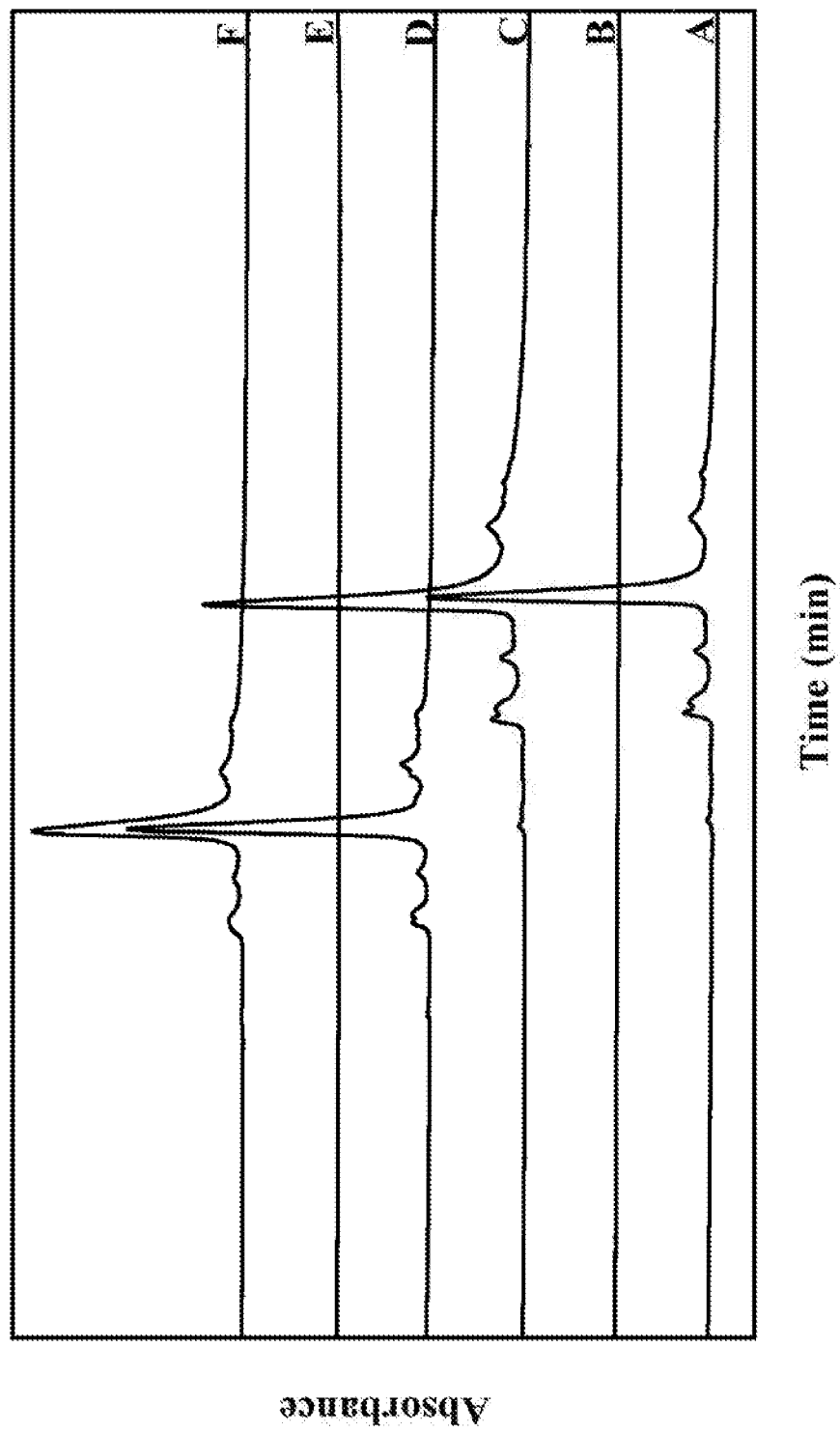
FIG. 8 depicts electropherograms of free homo-B mAb (trace A), homo-B mAb in the presence of either anti-chain-B mAb (trace B) or anti-chain-A mAb (trace C). Electropherograms of free homo-A mAb (trace D) and homo-A mAb in the presence of either anti-chain-A mAb (trace E) or anti-chain-B mAb (trace F) are also shown.

Experiments were run and data was collected for bsAb3-anti-B complex under ACE and PF-ACE conditions. Residual bsAb3 peaks that were observed under ACE conditions due to dissociation of analyte-ligand complex were not detected in PF-ACE conditions (FIG. 7). Under ACE conditions, once the analyte dissociates from analyte-ligand complex it can no longer form the complex again. Under PF-ACE conditions, the migration of analyte through the ligand plug allows the analyte to re-form analyte-ligand complex even if the analyte is dissociated earlier. The homo-B peaks that were observed in the absence of an affinity ligand zone, were shifted and shown as loss of signal when PF-ACE was performed with anti-B mAb (FIG. 8, traces A and B). This effect is due to homo-B-anti-B mAb complex formation. In contrast, the migration of the homo-B mAb through a capillary partially filled with an anti-A mAb remains unchanged relative to the trace that contains no affinity ligand zone, as homo-B mAb does not bind anti-A mAb (FIG. 8, traces A, C). Similarly, mobility shifts were observed only for specific binding (i.e. homo-A+anti-A or homo-B+anti-B) and not by other ligands (FIG. 8, traces D and F). These results indicate that the PF-ACE assay is highly specific to chain specific ligand based mobility shifts.

Example 3: Detection and Quantification of Homodimer mAb in Bispecific Samples

Figure 9:
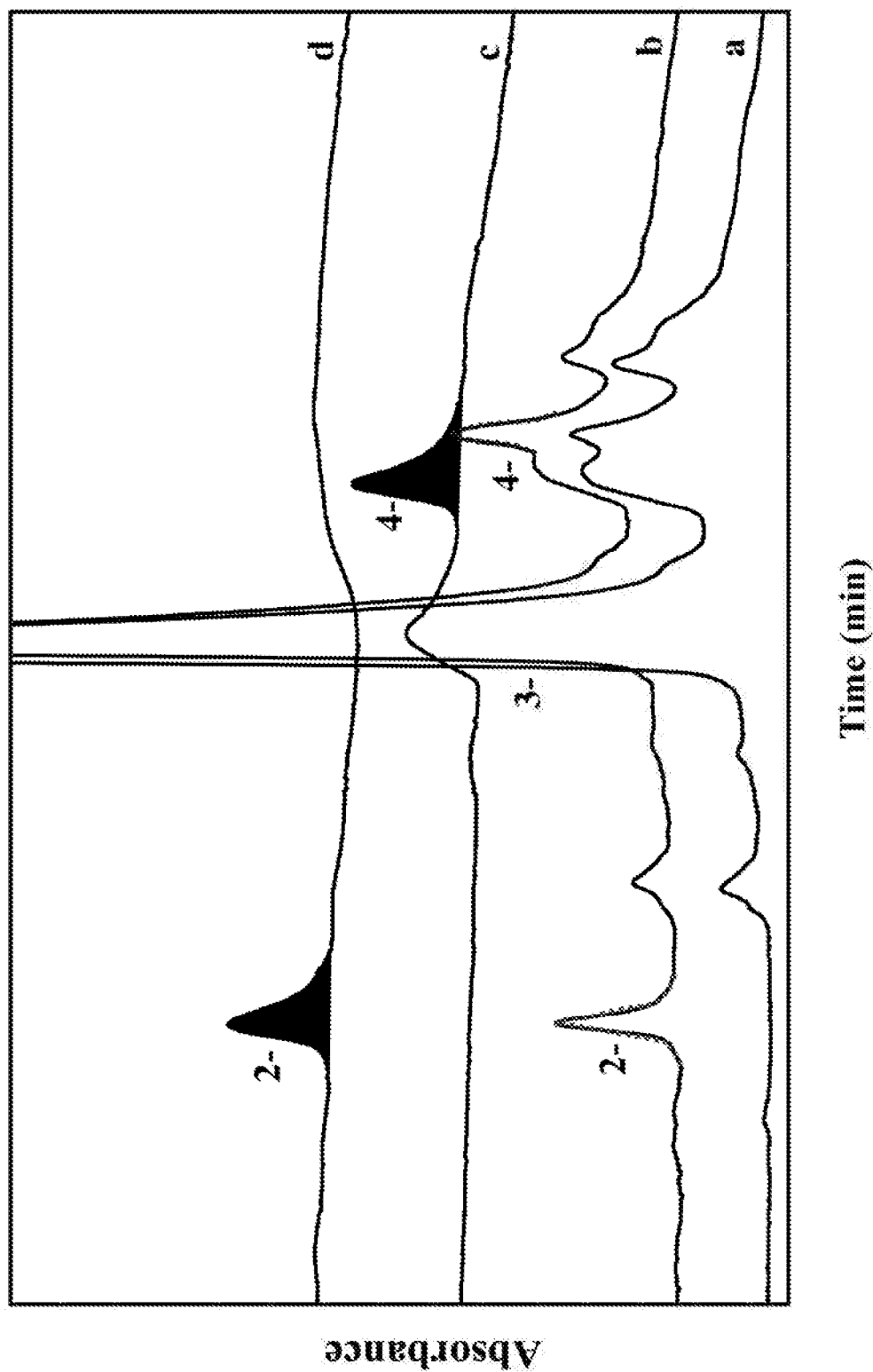
FIG. 9 depicts electropherograms of bsAb3 (trace a), and bsAb3 spiked with 5% of mAb impurities (trace b) in the presence of either anti-A mAb (trace c) or anti-B mAb (trace d).

To assess bsAb purity via PF-ACE assay, small amounts of (5%) of homo-A and homo-B were spiked into a bsAb3 sample to serve as homodimer "impurities". Resulting CZE and PF-ACE traces are shown in FIG. 9. Trace 'a' shows the electropherogram of bsAb3. Trace 'b' shows the electropherogram of bsAb3 spiked with 5% homo-A and homo-B impurities. Spiking of the homo-A and homo-B into bsAb3 resulted in an increase in the intensities of two peaks (compare trace a and trace b, peaks 2 and 4). Based on the electrophoretic mobilities of purified homodimers, these two peaks were tentatively identified, as homo-A and homo-B respectively. These identities were confirmed upon PF-ACE experiments in traces c and d. Trace d shows the bsAb3-anti-B PF-ACE where residual peaks would represent homo-A species. The residual peak observed in d has a migration time similar to peak 2 in trace b, thus verifying the identity of the peak in the spiked sample. Similar results were observed for bsAb3-anti-A PF-ACE (FIG. 9, trace c, homo-B). A small amount of residual peak observed in FIG. 9, trace c was excluded from the quantification as it corresponds to a contaminant observed in bsAb3 and it is not coming from the spiked samples. Based on PF-ACE, the amount of homo-A and homo-B present in spiked samples were estimated to be 5.2% and 5.2% respectively. These values are in good agreement with the spiked amount of 5% and are within the experimental errors.

Figure 10:
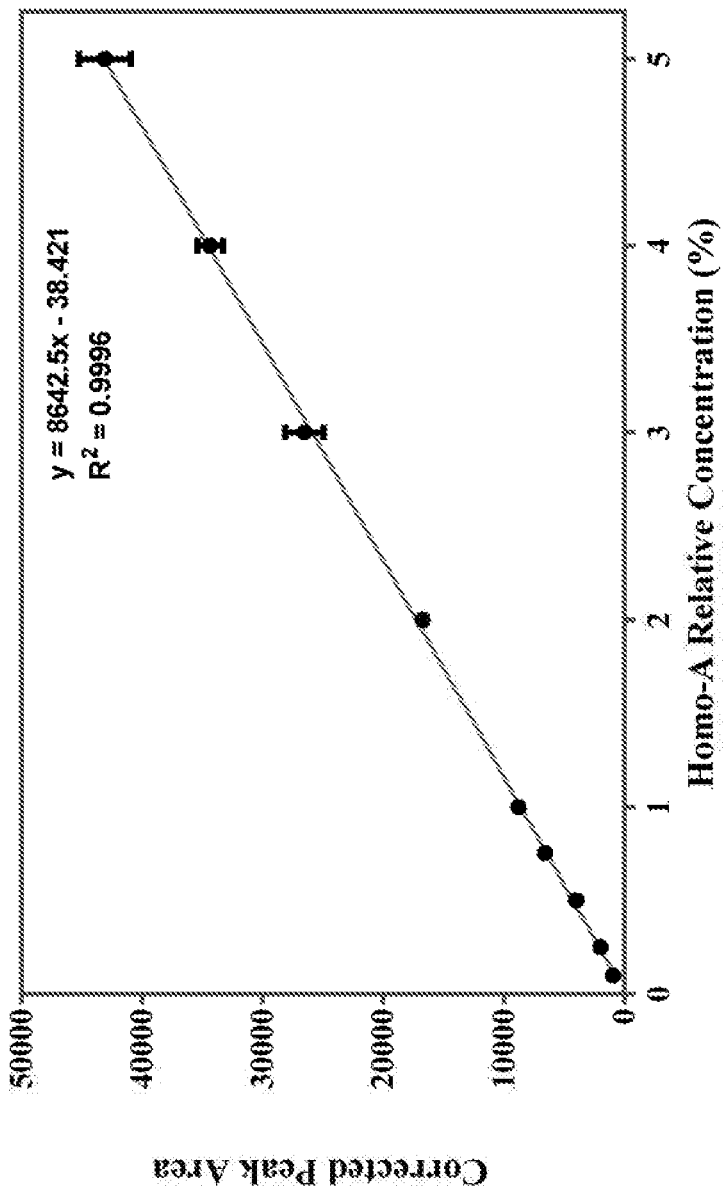
FIG. 10 depicts the corrected peak area for homodimer A (homo-A) over relative concentration (percent) of homo-A.
Figure 11:
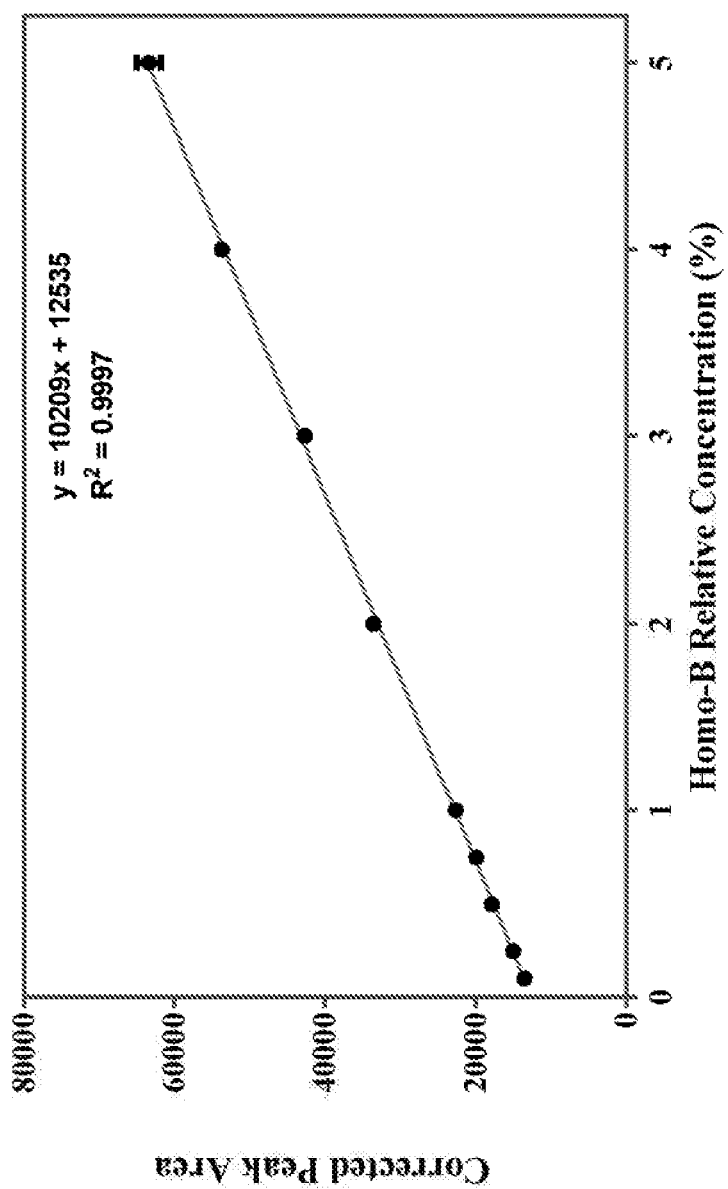
FIG. 11 depicts the corrected peak area for homodimer B (homo-B) over relative concentration (percent) of homo-B.

To assess limit of detection (LOD) and limit of quantification (LOQ), spike recovery was performed adding various amounts of homo-A and homo-B to purified bsAb3. Nine bsAb3 samples containing wide range of homo-A and homo-B mAbs (0.1%-5% by concentration) were prepared to study the level of homodimers present in these spiked samples. PF-ACE traces of bsAb3 containing homo-A and homo-B in the absence of an affinity ligand resulted in an electropherogram comprising peaks corresponding to bsAb3, homo-A and homo-B. The electropherograms indicate the existence of homodimeric mAbs in each spiked bsAb3 samples. Excellent linear response ($R^2$=0.999) was observed for homo-A (FIG. 10) and homo-B (FIG. 11) with increasing concentrations in spiked bsAb3 samples. Overall, the homodimer LOQ was experimentally determined to have a value of 0.1%.

Example 4: Protein Analysis Methodology

CZE experimentation was performed using a Beckman PA800 plus instrument equipped with diode array detector. 32 Karat® software (Beckman Coulter, Inc., Brea, CA) was used for data analysis. Briefly, antibody samples (1 mg/mL) were diluted with water to a concentration of approximately 1 mg/mL and injected at 0.5 psi for 45 seconds using a Beckman PA800 Plus with a bare fused silica capillary (total length of 60.2 cm, effective length of 50 cm, i.d. of 40 µm). ACE was performed under the same condition using a 1:2 molar ratio of bsAb to ligand. For PF-ACE analysis, the ligand plug (2 mg/mL of modified ligand in 1× phosphate buffered saline) was injected for 90 seconds at 1 psi prior to analyte or analyte-ligand complex injection. The separation was performed at 28 kV and the capillary temperature was maintained at 22° C. during separation. The samples were stored at 10° C. A buffer containing 600 mM ε-aminocaproic acid-acetic acid, 0.1% HPMC, pH 5.7 was used as a background electrolyte and 1 mM histidine was spiked as an internal standard.

BsAb, homo-A and homo-B samples were analyzed by CE-SDS under reducing conditions. BsAb and homodimers were co-expressed and purified from a single batch. Separation was performed on an Agilent Bioanalyzer and sample preparation generally followed the manufacturer's protocols for the Protein 230 kit.

The antibody, ligand and antibody-ligand complex samples were also analyzed based on size under native conditions by injection onto a WATERS ACQUITY UPLC system, equipped with ACQUITY UPLC BEH column (Waters Corporation, Milford, MA) that was equilibrated in SEC buffer (200 mM sodium phosphate, pH 7.1) at a flow rate of 0.3 mL/min.

The invention claimed is:

1. A composition, for separating and detecting a first protein from one or more other proteins, comprising:
   a first protein, wherein the first protein is a multisubunit protein,
   one or more other proteins, and
   a modified ligand that does not bind to the first protein but is capable of binding to the one or more other proteins to form a protein-ligand complex with a lower charge to mass ratio than the one or more other proteins without the modified ligand;
   wherein the modified ligand has a lower isoelectric point than an unmodified ligand and wherein the modified ligand comprises an acidic moiety.

2. The composition of claim 1, wherein the one or more other proteins is a multisubunit protein, and wherein the first protein and the one or more other proteins have similar charge to mass ratios.

3. The composition of claim 1, wherein the first protein comprises two identical first subunits, wherein the one or more other proteins comprises two identical second subunits or a combination of the first subunit and the second subunit, wherein the modified ligand is capable of binding to the second subunit.

4. The composition of claim 1, wherein the modified ligand comprises a covalent linkage with a lysine residue on the modified ligand.

5. The composition of claim 1, wherein the modified ligand comprises one or more amino acid sequences selected from the group consisting of SEQ ID NO:1, SEQ ID NO:2, SEQ ID NO:3, SEQ ID NO:7, SEQ ID NO:8 and SEQ ID NO:9.

6. The composition of claim 1, wherein the first protein is a first bivalent monospecific antibody and the mixture of proteins comprises a bispecific antibody and a second bivalent monospecific antibody.

7. A system comprising:
   a composition including a first protein, wherein the first protein is a multisubunit protein, one or more other proteins, and a modified ligand that does not bind to the first protein but is capable of binding to the one or more other proteins to form one or more protein-ligand complexes with a lower charge to mass ratio than the one or more other proteins without the modified ligand, wherein the modified ligand has a lower isoelectric point than an unmodified ligand and wherein the modified ligand comprises an acidic moiety;
   a capillary for housing the composition;
   a detector coupled to the capillary;
   an anode at or near one end of the capillary;
   a cathode at or near the other end of the capillary; and
   a power supply coupled to the capillary.

8. The system of claim 1, wherein the one or more other proteins is a multisubunit protein, and wherein the first protein and the one or more other proteins have similar charge to mass ratios.

9. The system of claim 7, wherein the modified ligand comprises a covalent linkage with a lysine residue on the modified ligand.

10. The system of claim 7, wherein the modified ligand comprises one or more amino acid sequences selected from the group consisting of SEQ ID NO:1, SEQ ID NO:2, SEQ ID NO:3, SEQ ID NO:7, SEQ ID NO:8 and SEQ ID NO:9.

11. The system of claim 7, wherein the detector is positioned near the cathode end of the capillary and the protein mixture is positioned in the capillary at the anode end of the capillary.

12. The system of claim 7, wherein the detector detects 200 nm to 280 nm light absorbance or laser induced fluorescence.

13. The system of claim 7, wherein the capillary comprises a ligand plug positioned between the anode and the detector, and the ligand plug comprises the modified ligand.

14. The system of claim 7, wherein the first protein is a first bivalent monospecific antibody and the mixture of proteins comprises a bispecific antibody and a second bivalent monospecific antibody.

* * * * *

UNITED STATES PATENT AND TRADEMARK OFFICE
CERTIFICATE OF CORRECTION

PATENT NO. : 12,158,473 B2  
APPLICATION NO. : 16/686770  
DATED : December 3, 2024  
INVENTOR(S) : Kathir Muthusamy et al.

Page 1 of 1

It is certified that error appears in the above-identified patent and that said Letters Patent is hereby corrected as shown below:

In the Claims

Column 34, Claim 8, Line 23 should read:  
8. The system of claim 7, wherein the one or more other Signed and Sealed this  
Twenty-fifth Day of March, 2025

Coke Morgan Stewart  
*Acting Director of the United States Patent and Trademark Office*

SEQUENCE LISTING

```
<160> NUMBER OF SEQ ID NOS: 20

<210> SEQ ID NO 1
<211> LENGTH: 12
<212> TYPE: PRT
<213> ORGANISM: artificial
<220> FEATURE:
<223> OTHER INFORMATION: synthetic

<400> SEQUENCE: 1

Tyr Thr Phe Thr Asn Tyr Trp Ile His Trp Glu Lys
1               5                   10

<210> SEQ ID NO 2
<211> LENGTH: 10
<212> TYPE: PRT
<213> ORGANISM: artificial
<220> FEATURE:
<223> OTHER INFORMATION: synthetic

<400> SEQUENCE: 2

Gly His Thr Glu Tyr Asn Gln Lys Phe Lys
1               5                   10

<210> SEQ ID NO 3
<211> LENGTH: 13
<212> TYPE: PRT
<213> ORGANISM: artificial
<220> FEATURE:
```

<223> OTHER INFORMATION: synthetic

<400> SEQUENCE: 3

His Phe Asp Tyr Trp Gly Gln Gly Thr Thr Leu Ile Val
1               5                   10

<210> SEQ ID NO 4
<211> LENGTH: 12
<212> TYPE: PRT
<213> ORGANISM: artificial
<220> FEATURE:
<223> OTHER INFORMATION: synthetic

<400> SEQUENCE: 4

Gln Ser Leu Val His Asn Asn Gly Asp Thr Phe Leu
1               5                   10

<210> SEQ ID NO 5
<211> LENGTH: 10
<212> TYPE: PRT
<213> ORGANISM: artificial
<220> FEATURE:
<223> OTHER INFORMATION: synthetic

<400> SEQUENCE: 5

Val Ser Asn Arg Phe Ser Gly Val Pro Asp
1               5                   10

<210> SEQ ID NO 6
<211> LENGTH: 13
<212> TYPE: PRT
<213> ORGANISM: artificial
<220> FEATURE:
<223> OTHER INFORMATION: synthetic

<400> SEQUENCE: 6

Gly Gly Thr Lys Leu Glu Ile Lys Arg Ala Asp Ala Ala
1               5                   10

<210> SEQ ID NO 7
<211> LENGTH: 12
<212> TYPE: PRT
<213> ORGANISM: artificial
<220> FEATURE:
<223> OTHER INFORMATION: Synthetic

<400> SEQUENCE: 7

Phe Thr Phe Asn Asn Tyr Ala Met Asn Trp Val Arg
1               5                   10

<210> SEQ ID NO 8
<211> LENGTH: 10
<212> TYPE: PRT
<213> ORGANISM: artificial
<220> FEATURE:
<223> OTHER INFORMATION: synthetic

<400> SEQUENCE: 8

Gly Asn Thr Tyr His Ala Asp Ser Val Lys
1               5                   10

<210> SEQ ID NO 9
<211> LENGTH: 13
<212> TYPE: PRT
<213> ORGANISM: artificial
<220> FEATURE:
<223> OTHER INFORMATION: synthetic

```
<400> SEQUENCE: 9

Gly Ala Phe Asp Ile Trp Gly Gln Gly Thr Met Val Thr
1               5                   10

<210> SEQ ID NO 10
<211> LENGTH: 12
<212> TYPE: PRT
<213> ORGANISM: artificial
<220> FEATURE:
<223> OTHER INFORMATION: synthetic

<400> SEQUENCE: 10

Gln Ser Val Phe Tyr Ser Ser Asn Lys Gln Asn Phe
1               5                   10

<210> SEQ ID NO 11
<211> LENGTH: 9
<212> TYPE: PRT
<213> ORGANISM: artificial
<220> FEATURE:
<223> OTHER INFORMATION: synthetic

<400> SEQUENCE: 11

Arg Ala Ser Thr Arg Glu Ser Gly Val
1               5

<210> SEQ ID NO 12
<211> LENGTH: 13
<212> TYPE: PRT
<213> ORGANISM: artificial
<220> FEATURE:
<223> OTHER INFORMATION: synthetic

<400> SEQUENCE: 12

Gly Gln Gly Thr Lys Val Glu Ile Lys Arg Ala Asp Ala
1               5                   10

<210> SEQ ID NO 13
<211> LENGTH: 128
<212> TYPE: PRT
<213> ORGANISM: artificial
<220> FEATURE:
<223> OTHER INFORMATION: synthetic

<400> SEQUENCE: 13

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Gly Ser Ser Gly Ser Gly Gly Asn Thr Tyr His Ala Asp Ser Val
    50                  55                  60

Lys Gly Arg Phe Thr Ile Ser Arg Asp Asn Asn Asn Ala Leu Tyr
65                  70                  75                  80

Leu Gln Met Asn Ser Leu Arg Ala Glu Asp Thr Ala Val Tyr Phe Cys
                85                  90                  95

Ala Lys Gln Gly Asp Trp Asn Trp Gly Ala Phe Asp Ile Trp Gly Gln
            100                 105                 110

Gly Thr Met Val Thr Val Ser Ser Ala Lys Thr Thr Ala Pro Ser Val
        115                 120                 125
```

```
<210> SEQ ID NO 14
<211> LENGTH: 128
<212> TYPE: PRT
<213> ORGANISM: artificial
<220> FEATURE:
<223> OTHER INFORMATION: synthetic

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Phe Tyr Ser
            20                  25                  30

Ser Asn Lys Gln Asn Phe Ile Ala Trp Tyr Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Val Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Ser Pro Pro Thr Phe Gly Gln Gly Thr Lys Val Glu Ile
            100                 105                 110

Lys Arg Ala Asp Ala Ala Pro Thr Val Ser Ile Phe Pro Pro Ser Ser
        115                 120                 125

<210> SEQ ID NO 15
<211> LENGTH: 450
<212> TYPE: PRT
<213> ORGANISM: artificial
<220> FEATURE:
<223> OTHER INFORMATION: synthetic

<400> SEQUENCE: 15

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Gly Ser Ser Gly Ser Gly Asn Thr Tyr His Ala Asp Ser Val
    50                  55                  60

Lys Gly Arg Phe Thr Ile Ser Arg Asp Asn Ser Asn Asn Ala Leu Tyr
65                  70                  75                  80

Leu Gln Met Asn Ser Leu Arg Ala Glu Asp Thr Ala Val Tyr Phe Cys
                85                  90                  95

Ala Lys Gln Gly Asp Trp Asn Trp Gly Ala Phe Asp Ile Trp Gly Gln
            100                 105                 110

Gly Thr Met Val Thr Val Ser Ser Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190
```

```
Ser Thr Trp Pro Ser Gln Ser Ile Thr Cys Asn Val Ala His Pro Ala
            195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
                260                 265                 270

Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
        370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
                435                 440                 445

Gly Lys
    450

<210> SEQ ID NO 16
<211> LENGTH: 219
<212> TYPE: PRT
<213> ORGANISM: artificial
<220> FEATURE:
<223> OTHER INFORMATION: synthetic

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Phe Tyr Ser
            20                  25                  30

Ser Asn Lys Gln Asn Phe Ile Ala Trp Tyr Gln Gln Lys Pro Gly Gln
        35                  40                  45

Pro Pro Lys Leu Leu Ile Tyr Arg Ala Ser Thr Arg Glu Ser Gly Val
    50                  55                  60

Pro Asp Arg Phe Ser Gly Ser Gly Ser Val Asp Phe Thr Leu Thr
65                  70                  75                  80

Ile Ser Ser Leu Gln Ala Glu Asp Val Ala Val Tyr Tyr Cys Gln Gln
                85                  90                  95
```

His Tyr Ser Ser Pro Pro Thr Phe Gly Gln Gly Thr Lys Val Glu Ile
            100                 105                 110

Lys Arg Ala Asp Ala Ala Pro Thr Val Ser Ile Phe Pro Pro Ser Ser
            115                 120                 125

Glu Gln Leu Thr Ser Gly Gly Ala Ser Val Val Cys Phe Leu Asn Asn
130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
                165                 170                 175

Ser Thr Tyr Ser Met Ser Ser Thr Leu Thr Leu Thr Lys Asp Glu Tyr
                180                 185                 190

Glu Arg His Asn Ser Tyr Thr Cys Glu Ala Thr His Lys Thr Ser Thr
                195                 200                 205

Ser Pro Ile Val Lys Ser Phe Asn Arg Gly Glu
            210                 215

<210> SEQ ID NO 17
<211> LENGTH: 128
<212> TYPE: PRT
<213> ORGANISM: artificial
<220> FEATURE:
<223> OTHER INFORMATION: synthetic

<400> SEQUENCE: 17

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Asn Tyr
            20                  25                  30

Trp Ile His Trp Glu Lys Gln Arg Pro Glu Gln Gly Leu Glu Trp Ile
        35                  40                  45

Gly Tyr Ile Asn Pro Asn Thr Gly His Thr Glu Tyr Asn Gln Lys Phe
    50                  55                  60

Lys Asp Lys Ala Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Thr Tyr Ser Gly Ser Ser His Phe Asp Tyr Trp Gly Gln Gly
            100                 105                 110

Thr Thr Leu Ile Val Ser Ser Ala Lys Thr Thr Pro Pro Ser Val Tyr
            115                 120                 125

<210> SEQ ID NO 18
<211> LENGTH: 128
<212> TYPE: PRT
<213> ORGANISM: artificial
<220> FEATURE:
<223> OTHER INFORMATION: synthetic

<400> SEQUENCE: 18

Asp Ile Val Met Thr Gln Thr Pro Val Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asp Thr Phe Leu His Trp Tyr Leu Gln Lys Pro Gly Gln Ser
            35                  40                  45

Pro Lys Leu Leu Ile Tyr Lys Val Ser Asn Arg Phe Ser Gly Val Pro

```
            50                  55                  60
Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Thr
                 85                  90                  95

Thr Leu Ile Pro Arg Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125
```

<210> SEQ ID NO 19
<211> LENGTH: 443
<212> TYPE: PRT
<213> ORGANISM: artificial
<220> FEATURE:
<223> OTHER INFORMATION: synthetic

<400> SEQUENCE: 19

```
Gln Val Gln Leu Gln Gln Ser Gly Ala Glu Leu Ala Lys Pro Gly Ala
  1               5                  10                  15

Ser Val Lys Met Ser Cys Lys Ala Ser Gly Tyr Thr Phe Thr Asn Tyr
                 20                  25                  30

Trp Ile His Trp Glu Lys Gln Arg Pro Glu Gln Gly Leu Glu Trp Ile
             35                  40                  45

Gly Tyr Ile Asn Pro Asn Thr Gly His Thr Glu Tyr Asn Gln Lys Phe
         50                  55                  60

Lys Asp Lys Ala Thr Leu Thr Ala Asp Arg Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Thr Tyr Ser Gly Ser Ser His Phe Asp Tyr Trp Gly Gln Gly
                100                 105                 110

Thr Thr Leu Ile Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
                260                 265                 270

Trp Phe Val Asp Asp Val Glu Val His Thr Ala Gln Thr Gln Pro Arg
            275                 280                 285

Glu Glu Gln Phe Asn Ser Thr Phe Arg Ser Val Ser Glu Leu Pro Ile
```

```
                290                 295                 300
Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 20
<211> LENGTH: 219
<212> TYPE: PRT
<213> ORGANISM: artificial
<220> FEATURE:
<223> OTHER INFORMATION: synthetic

<400> SEQUENCE: 20

Asp Ile Val Met Thr Gln Thr Pro Val Ser Leu Pro Val Ser Leu Gly
1               5                   10                  15

Asp Gln Ala Ser Ile Ser Cys Arg Ser Ser Gln Ser Leu Val His Asn
                20                  25                  30

Asn Gly Asp Thr Phe Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Thr
                85                  90                  95

Thr Leu Ile Pro Arg Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190
```

```
Arg His Asn Ser Tyr Thr Cys Glu Ala Thr His Lys Thr Ser Thr Ser
        195                 200                 205

Pro Ile Val Lys Ser Phe Asn Arg Gly Glu Cys
    210                 215
```